United States Patent [19]
Carman et al.

[11] Patent Number: 5,595,739
[45] Date of Patent: Jan. 21, 1997

[54] HEPATITIS B VIRUS MUTANTS, REAGENTS AND METHODS FOR DETECTION

[75] Inventors: William F. Carman, Glasgow, United Kingdom; Richard H. Decker, Deerfield, Ill.; Lesley Wallace, Glasgow, United Kingdom; Larry T. Mimms, Lake Villa; Larry R. Solomon, Mundelein, both of Ill.

[73] Assignee: Abbott Laboratories, Abbott Park, Ill.

[21] Appl. No.: 59,031

[22] Filed: May 7, 1993

[51] Int. Cl.$^6$ .................... A61K 39/29; G01N 33/543; C07K 14/02; C12Q 1/70
[52] U.S. Cl. .................... 424/189.1; 424/227.1; 435/5; 435/975; 435/235.1; 530/324; 530/350; 530/403; 930/220
[58] Field of Search .................... 424/89, 189.1, 424/227.1; 514/12, 25; 530/324, 403, 350; 935/65; 435/5, 975, 235.1; 436/518; 930/220

[56] References Cited

U.S. PATENT DOCUMENTS 5,279,944  1/1994  Fabrizi et al. .................... 435/5

FOREIGN PATENT DOCUMENTS 0511855  11/1992  European Pat. Off. .
9114703  10/1991  WIPO .

OTHER PUBLICATIONS

Hiroaki Okamoto et al., "The Loss of Subtypic Determinants in Alleles, *d/y* Or *w/r*, On Hepatitis B Surface Antigen" *Molecular Immunology*, vol. 26, No. 2, pp. 197–205 (1989).

William Carman, et al, "Viral genetic variation: hepatitis B virus as a clinical example" *The Lancet*, vol. 341:349–353 (1993).

William F. Carman, et al, "Vaccine–induced escape mutant of hepatitis B virus." *Medical Science* vol. 336:325–329 (1990).

Tim J. Harrison et al., "Variants of Hepatitis B Virus" *Vox Sang* 1992; 63:161–167.

K. Yamamoto, et al., "Naturally Occurring Escape Mutants of Hepatitis B Virus with Various Mutations in the S Gene in Carriers Seropositive for Antibody to Hepatitis B Surface Antigen", *J. Virol.*, vol. 68 No. 4:2671–2676 (1994).

W. F. Carman, et al., "Genetic Variation in Hepatitis B Virus", *Gastroenterology*, vol. 102:711–719 (1992).

Ashton–Rickardt, P. et al, "Mutants of the Hepatitis B Virus Surface Antigen That Define Some Antigenically Essential Residues in the Immunodominant *a* Region", *Journal of Medical Virology*, 29:196–203 (1989).

*Primary Examiner*—Mary E. Mosher
*Attorney, Agent, or Firm*—Priscilla E. Porembski

[57] ABSTRACT

Mutant Hepatitis B Virus (HBV) nucleic acid sequences useful for a variety of diagnostic and therapeutic applications, kits for using the HBV nucleic acid sequences, HBV immunogenic particles, and a method for producing antibodies to HBV. Also provided are methods for producing antibodies, polyclonal or monoclonal, from the HBV nucleic acid sequences.

11 Claims, No Drawings

HEPATITIS B VIRUS MUTANTS, REAGENTS AND METHODS FOR DETECTION

BACKGROUND OF THE INVENTION

This invention relates generally to mutants of Hepatitis B Virus (HBV), and more particularly, relates to new mutants of HBV, their significance in clinical applications, their use as reagents in detection of HBV infection and immunity and their use in vaccines.

HBV is known to cause a variety of disease states, from mild subclinical infection to chronic active and fulminant hepatitis. The hepatitis B genome is a circular, partially double stranded DNA of approximately 3200 base pairs which code for seven viral proteins. P. Tiollais et al., *Nature* 317:489–495 (1985). The polymerase gene completely overlaps the viral envelope genes PreS1, PreS2 and S, and partially overlaps the X and core genes. The envelope of the hepatitis B virion consists of three proteins and their glycosylated derivatives. These proteins, termed small (S), middle (M) and large (L) hepatitis B surface (HBs) proteins contain the S gene sequence. W. H. Gerlich et al., in *Viral Hepatitis and Liver Disease*, F. B. Hollinger et al., eds. Williams-Wilkens, Baltimore, Md., pages 121–134 (1991). The MHBs contains the PreS2 sequence (55 amino acids [a.a]) and the L protein contains the Pros1 sequence (108 or 119 a.a., depending on subtype) plus the PreS2 sequence. Only a very small portion of the total hepatitis B surface antigen exists as complete virions or Dane particles. Two other morphological forms, 22 nm spherical particles and filaments of 22 nm diameter and variable length, lack capsid or DNA and are produced in high excess over HBV virions.

The core gene encodes the nucleocapsid protein (183 or 185 a.a.), hepatitis B core Antigen (HBcAg). Immediately upstream of the core gene is the precore region which consists of 87 nucleotides encoding 29 a.a. in phase with the core gene. The first 19 a.a. of the precore region serve as a signal for membrane translocation and eventual secretion of the precore gene product, termed HBe antigen (Ag). The function of HBe is enigmatic but may help the virus escape immune surveillance by inducing immune tolerance.

Because of the genomic compactness and the extensive functional overlaps, it is expected that significant constraints on DNA sequence divergence would occur in order to maintain a genome capable of efficient replication and transmission. The hepatitis B virus, however, shows greater mutability than previously appreciated. Similar to the Human Immunodeficiency Virus (HIV), HBV uses reverse transcriptase (RT) as an essential step in the replication cycle. RT has poor proofreading ability, leading to a high rate of nucleotide misincorporation. Calculations suggest that this error-prone replication leads to one point replacement, deletion or insertion per 1000 to 100,000 nucleotides copied. W. Carman et al., *Lancet* 341:349–353 (1993). Variability in the virus was first discovered through classical subtyping studies of HBsAg. A. M. Courouce et al., *Bibliotheca Haematologica* 42:1 (1976).

Mutations may not be located randomly on the genome. Recent reports have documented the emergence of other mutations in the pre core, core and envelope protein genes, PreS and S, which presumably give these mutants a selective advantage over wild type (WT) in evading the immune system.

Evidence suggests that viral clearance and liver cell injury in HBV infection are mediated by a cytotoxic T lymphocyte (CTL) response to one or more HBV-encoded antigens expressed at the hepatocyte surface. M. Peters et al., *Hepatology* 13:977–994 (1991). A strong T-cell response to HBcAg and HBeAg antigens, but not to envelope antigens, was found in acute hepatitis B. Persistence of viral replication correlated with a blunted T-cell response to HBcAg. Although T cell response to viral antigen may be abrogated in chronic HBV, CTL response may persist in chronic carriers.

Also, there is evidence of ongoing humoral response in both symptomatic and asymptomatic hepatitis B carders. High levels of anti-HBc are observed in almost all HBV carriers. Twenty percent of random HBsAg positive specimens have detectable HBeAg and anti-HBe, and 10–20% have detectable but low level anti-HBs. A recent report using very sensitive detection methods indicates that virtually all HBV patients with liver disease and about 50% of chronic hepatitis B patients without liver disease have demonstrable humoral immune responses specific for HBeAg and anti-HBsAg and PreS Ag. Much of the anti-HBs response, however, may exist because of the different fine specificities of HBsAg and anti-HBs and probably is not neutralizing. These data support the theory that there is ongoing immune surveillance of precore, core and envelope gene products in chronic HBV carriers which could provide selective pressure for the emergence of HBV variants.

The HBV envelope regions encompassing PreS1 and PreS2 and the region 120–160 a.a. of S are exposed on the surface of the viral particles, and thus would be expected to be targets of immune surveillance. W. H. Gerlich et al., supra. Some S mutants described to date have significantly affected the antigenicity of the "a" epitope(s) which is common or group-specific determinant(s) of SHBs. W. Carman et al., *Gastroenterology* 102:711–719 (1992). The "a" determinants are complex, conformational and dependent upon disulfide bonding among highly conserved cysteine residues. The "a" immunoreactivity can be partially mimicked by cyclic synthetic peptides. Although the "a" epitope(s) traditionally had been defined by reactivity to polyclonal antisera, the use of monoclonal antibody has shown that the "a" region consists of at least five non-overlapping epitopes. D. Peterson et al., *J. Immunol.* 132:920–927 (1984). Genetic variation in the "a" determinant leading to immune escape has been described in vacinees in Italy and Japan and in liver transplant patients on monoclonal anti-a antibody therapy. See, for example, W. F. Carman et al., *Lancet* 336:325–329 (1990); H. Okamoto et al., *Pediatric Research* 32:264–268 (1992); G. McMahon et al., *Hepatology* 15:757–766 (1992); H. Fujii et al., *Biochem. Biophys. Res. Comm.* 184:1152–1157 (1992); and T. J. Harrison et al., *J. of Hepatology* 13:5105–5107 (1991). The most common mutant described to date is a single nucleotide substitution leading to replacement of a glycine with an arginine (G-R 145). This mutation destroys some but not all "a" epitopes. Detection of anti-HBs with monoclonal antibody has not been problematic.

Other mutations in the "a" region lead to loss of subtypic or type specific determinants, y/d and w/r. Several recent papers have documented the emergence of gross deletions and point mutations in the PreS1/PreS2 region suggesting that the production of these envelope gene products also are under immune selection in chronically infected individuals. HBV mutants which cannot replicate because of deletions in the env, C or P genes have been reported in plasma from HBV carriers. All coexist with HBV forms which are replication competent. Okamoto et al. (supra) demonstrated that mutant genomes with gross deletions in the PreS/S, C and P genes derived from plasma or asymptomatic carriers may be complemented in transient expressions system with hepatoma cells. Complementation was measured as the ability to secrete viral particles with mutant genomes into the culture media. Interestingly, all routants had an intact encapsidation signal. Complementation with predecessor WT viruses, other routants and even with HBV DNA sequences integrated into host chromosomes was demonstrated in this in vitro system. Thus, the suggestion that HBV mutants acting as defective interfering particles may attenuate WT virus replication and thereby help maintain persistence of infection has been made.

The detection of mutants of Hepatitis B surface antigen therefore is important. Mutants may develop over time due to such factors as vaccine administration or infection. The identification and detection of mutant Hepatitis B Virus(es) may lead to vaccine development and detection systems to determine the presence of these mutants in test samples. A need therefore exists not only to identify these mutant strains, but also to provide detection systems capable of determining the presence of the mutant in a test sample. A further need also exists for the development of a vaccine to such mutant swain(s).

SUMMARY OF THE INVENTION

This invention describes a mutant Hepatitis B Virus having a modified "a" determinant in which there is an insertion of two amino acids at the 122 position of the HBsAg sequence, which insertion corresponds to a six nucleotide insertion at the 366 position of the HBsAg genome. The two amino acids inserted at position 122 are N and T, while the corresponding nucleotide sequence appearing at position 366 of the nucleotide sequence is -A-A-C-A-C-A-.

This invention provides a purified polynucleotide of mutant HBV comprising a modified "a" determinant in which there is an insertion of at least six nucleotides at position 366 of the HBsAg genome, a recombinant polynucleotide of mutant HBV comprising a modified "a" determinant in which there is an insertion of at least two amino acids at position 122 of the HBsAg sequence, host cells and recombinant vectors reciting this insertion. The two amino acids inserted at position 122 are N and T, while the corresponding nucleotide sequence appearing at position 366 of the nucleotide sequence is -A-A-C-A-C-A-. The recombinant polynucleotide of mutant HBV comprises a sequence derived from a mutant HBV genome. Also, the recombinant polynucleotide of mutant HBV comprises an epitope of mutant HBV. The invention also provides a recombinant expression system comprising an open reading frame of DNA derived from the genome of mutant HBV, wherein the open reading frame is operably linked to a control sequence compatible with a desired host, cells transformed with said recombinant expression system and polypeptides produced by said cells. The invention further provides purified mutant HBV, which can comprise a preparation of mutant HBV polypeptide. All embodiments recite the modification of the "a" determinant having either at least a two-amino insertion at amino acid 122 or a six nucleotide insertion at 366.

Additionally, the present invention provides a recombinant polypeptide comprising a sequence derived from a mutant HBV genome, and a recombinant polypeptide comprising a mutant HBV epitope. Also provided is an antibody directed against at least one epitope of mutant HBV. The antibody is polyclonal or monoclonal. The invention further provides a fusion polypeptide comprising a polypeptide of mutant HBV.

The invention also provides a particle that is immunogenic against mutant HBV infection, comprising a non-mutant HBV polypeptide having an amino acid sequence capable of forming a particle when said sequence is produced in a eukaryotic or prokaryotic host, and an epitope of mutant HBV, a polynucleotide probe for mutant HBV, and various test kits for performing various methods to detect either mutant HBV antigen or mutant HBV antibody.

Moreover, the invention provides a method for producing a polypeptide containing an epitope of mutant HBV comprising incubating host cells transformed with an expression vector containing a sequence encoding a polypeptide containing an epitope of HBV, under conditions and for a time which allows expression of said polypeptide.

Further, a method for detecting mutant HBV nucleic acids in a test sample suspected of containing mutant HBV is provided, wherein the method comprises reacting the test sample with a probe for a polynucleotide of mutant HBV under conditions and for a time which allows the formation of a complex between the probe and the nucleic acid of mutant HBV in the test sample; and detecting the complex which contains the probe. An additional method for detecting mutant HBV antigen in a test sample suspected of containing mutant HBV comprises contacting a test sample with an antibody directed against mutant HBV antigen to be detected for a time and under conditions sufficient to allow the formation of antibody/antigen complexes; and detecting said complex containing the antibody. Still another method for detecting mutant HBV antibodies in a test sample suspected of containing said antibodies, comprises contacting the test sample with a probe polypeptide wherein said polypeptide contains a mutant HBV epitope, for a time and under conditions sufficient to allow antigen/antibody complexes to form; and detecting said complexes which contain the probe polypeptide.

A vaccine for treatment of mutant HBV infection also is provided which comprises a pharmacologically effective dose of an immunogenic mutant HBV polypeptide which contains an epitope of mutant HBV in a pharmaceutically acceptable excipient. The vaccine for treatment of mutant HBV infection also can comprise an inactivated or attenuated mutant HBV in a pharmacologically effective dose in an pharmaceutically acceptable excipient.

Further, the invention provides tissue culture grown cells infected with mutant HBV and a method for producing antibodies to mutant HBV comprising administering to an individual an isolated immunogenic polypeptide containing an epitope of mutant HBV in an amount sufficient to produce an immune response.

DETAILED DESCRIPTION OF THE INVENTION

The present invention provides characterization of a newly ascertained mutant of HBV that has a two amino acid (N-T) insertion at position 122 of the HBV envelope region. The present invention provides methods for determining the presence of the mutant HBV in a test sample, and reagents useful in these methods. All aspects provide a modification of the "a" determinant in which there is an insertion of two amino acids at position 122 of the HBsAg sequence, which corresponds to a six nucleotide insertion at position 366 of the HBsAg genome.

The nucleic acid sequence derived from mutant HBV, or a portion thereof are useful as probes to determine the presence of mutant HBV in test samples. The sequence also makes available polypeptide sequences of mutant HBV antigen(s) encoded within the genome(s) of such mutant HBV and permits the production of polypeptides which are useful as standards or reagents in diagnostic tests and/or as components of vaccines. Monoclonal and polyclonal antibodies directed against an epitope contained within these polypeptide sequences, also are useful for diagnostic tests as well as therapeutic agents, for screening of antiviral agents, and for the isolation of the mutant HBV from which these nucleic acid sequences are derived.

According to one aspect of the invention, there will be provided a purified polynucleotide of mutant HBV, a recombinant polynucleotide of mutant HBV, a recombinant polynucleotide comprising a sequence derived from a genome of mutant HBV; a recombinant polypeptide encoding an epitope of mutant HBV; a recombinant vector containing any of the above described recombinant polypeptides, and a host cell transformed with any of these vectors. All aspects provide a modification of the "a" determinant in which there is an insertion of two amino acids at position 122 of the HBsAg sequence, which corresponds to a six nucleotide insertion at position 366 of the HBsAg genome.

In another aspect of the invention there will be provided purified antigen of mutant HBV; a preparation of polypeptides from the purified mutant HBV; a purified polypeptide of mutant HBV; a purified polypeptide comprising an epitope which is immunologically identifiable with an epitope contained in mutant HBV.

In yet another aspect of the invention there will be provided a recombinant expression system comprising an open reading frame (ORF) of DNA derived from a mutant HBV genome, wherein the ORF is operably linked to a control sequence compatible with a desired host, a cell transformed with the recombinant expression system, and a polypeptide produced by the transformed cell.

Additional aspects of the present invention include a recombinant polypeptide of mutant HBV, a recombinant polypeptide comprised of a sequence derived from a genome of mutant HBV; a recombinant polypeptide comprised of an epitope of mutant HBV and a fusion polypeptide comprised of a polypeptide of mutant HBV.

The present invention also provides methods for producing a monoclonal antibody which specifically binds to at least one epitope of mutant HBV; a purified preparation of polyclonal antibodies which specifically bind to at least one mutant HBV epitope; and methods for using these antibodies, which include diagnostic, prognostic and therapeutic uses.

In still another aspect of the invention there will be provided a particle which is immunogenic against mutant HBV infection comprising a non-mutant HBV polypeptide having an amino acid sequence capable of forming a particle when said sequence is produced in a eukaryotic host, and an epitope of mutant HBV.

A polynucleotide probe for mutant HBV also will be provided.

The present invention provides kits containing reagents which can be used for the detection of the presence and/or amount of polynucleotides derived from mutant HBV, such reagents comprising a polynucleotide probe containing a nucleotide sequence from mutant HBV of about 8 or more nucleotides in a suitable container and which nucleotides encode for the insertion of at least two amino acids at position 122; a reagent for detecting the presence and/or amount of a mutant HBV antigen comprising an antibody directed against the mutant HBV antigen to be detected in a suitable container; a reagent for detecting the presence and/or amount of antibodies directed against a mutant HBV antigen comprising a polypeptide containing an epitope of mutant HBV present in the mutant HBV antigen, provided in a suitable container. Other kits for various assay formats also are provided by the present invention as described herein.

Other aspects of the present invention include a polypeptide comprising an epitope of mutant HBV attached to a solid phase and an antibody to an epitope of mutant HBV attached to a solid phase. Also included are methods for producing a polypeptide containing an epitope to mutant HBV comprising incubating host cells transformed with an expression vector containing a sequence encoding a polypeptide containing an epitope of mutant HBV under conditions which allow expression of the polypeptide, and a polypeptide containing an epitope of mutant HBV produced by this method.

The present invention also provides assays which utilize the recombinant or synthetic polypeptides provided by the invention, as well as the antibodies described herein in various formats, any of which may employ a signal generating compound in the assay. Assays which do not utilize signal generating compounds to provide a means of detection also are provided. All of the assays described generally detect either antigen or antibody, or both, and include contacting a test sample with at least one reagent provided herein to form at least one antigen/antibody complex and detecting the presence of the complex. These assays are described in detail herein.

Vaccines for treatment of mutant HBV infection comprising an immunogenic peptide containing a mutant HBV epitope, or an inactivated preparation of mutant HBV, or an attenuated preparation of mutant HBV are included in the present invention. Also included in the present invention is a method for producing antibodies to mutant HBV comprising administering to an individual an isolated immunogenic polypeptide containing an epitope of mutant HBV in an amount sufficient to produce an immune response in the inoculated individual.

Also provided by the present invention is a tissue culture grown cell infected with mutant HBV.

Definitions

Note: All definitions include the modification of the "a" determinant in which there is an insertion of two amino acids at position 122 of the HBsAg sequence, which corresponds to a six nucleotide insertion at position 366 of the HBsAg genome. The term "mutant HBV" means a viral isolate having this modification of the "a" determinant.

A polynucleotide "derived from" a designated sequence from the mutant HBV genome refers to a polynucleotide sequence which is comprised of a sequence of approximately at least about 6 nucleotides, is preferably at least about 8 nucleotides, is more preferably at least about 10–12 nucleotides, and even more preferably is at least about 15–20 nucleotides corresponding, i.e., homologous to or complementary to, a region of the designated nucleotide sequence. Preferably, the sequence of the region from which the polynucleotide is derived is homologous to or complementary to a sequence which is unique to the mutant HBV genome. Whether or not a sequence is complementary to or homologous to a sequence which is unique to a mutant HBV genome can be determined by techniques known to those skilled in the art. Comparisons to sequences in databanks, for example, can be used as a method to determine the uniqueness of a designated sequence.

The derived polynucleotide will not necessarily be derived physically from the nucleotide sequence of mutant HBV, but may be generated in any manner, including but not limited to chemical synthesis, replication or reverse transcription or transcription, which are based on the information provided by the sequence of bases in the region(s) from which the polynucleotide is derived. In addition, combinations of regions corresponding to that of the designated sequence may be modified in ways known in the art to be consistent with an intended use.

A polypeptide or amino acid sequence derived from a designated nucleic acid sequence or from the mutant HBV genome refers to a polypeptide having an amino acid sequence identical to that of a polypeptide encoded in the sequence, or a portion thereof wherein the portion consists of at least 2 to 5 amino acids, and more preferably at least 8 to 10 amino acids, and even more preferably 15 to 20 amino acids, or which is immunologically identifiable with a polypeptide encoded in the sequence.

A "recombinant protein" ("recombinant polynucleotide") as used herein means at least a polypeptide of genomic, semisynthetic or synthetic origin which by virtue of its origin or manipulation is not associated with all or a portion of the polynucleotide with which it is associated in nature or in the form of a library and/or is linked to a polynucleotide other than that to which it is linked in nature. A recombinant or derived polypeptide is not necessarily translated from a designated nucleic acid sequence of mutant HBV or from a mutant HBV genome. It also may be generated in any manner, including chemical synthesis or expression of a recombinant expression system, or isolation from mutated HBV.

The term "polynucleotide" as used herein means a polymeric form of nucleotides of any length, either ribonucleotides or deoxyribonucleotides. This term refers only to the primary structure of the molecule. Thus, the term includes double- and single-stranded DNA, as well as double- and single-stranded RNA. It also includes modifications, either by methylation and/or by capping, and unmodified forms of the polynucleotide.

"Purified viral polynucleotide" refers to a genome of mutant HBV or fragment thereof which is essentially free, i.e., contains less than about 50%, preferably less than about 70%, and even more preferably, less than about 90% of polypeptides with which the viral polynucleotide is naturally associated. Techniques for purifying viral polynucleotides are well known in the art and include, for example, disruption of the particle with a chaotropic agent, and separation of the polynucleotide(s) and polypeptides by ion-exchange chromatography, affinity chromatography, and sedimentation according to density. Thus, "purified viral polypeptide" means a polypeptide of mutant HBV or fragment thereof which is essentially free, that is, contains less than about 50%, preferably less than about 70%, and even more preferably, less than about 90% of of cellular components with which the viral polypeptide is naturally associated. Methods for purifying are known to the routineer.

"Polypeptide" as used herein indicates a molecular chain of amino acids and does not refer to a specific length of the product. Thus, peptides, oligopeptides, and proteins are included within the definition of polypeptide. This term however is not intended to refer to post-expression modifications of the polypeptide, for example, glycosylations, acetylations, phosphorylations and the like.

"Recombinant host cells," "host cells," "cells," "cell lines," "cell cultures," and other such terms denoting microorganisms or higher eucaryotic cell lines cultured as unicellular entities refer to cells which can be, or have been, used as recipients for recombinant vector or other transfer DNA, and include the original progeny of the original cell which has been transfected.

As used herein "replicon" means any genetic element, such as a plasmid, a chromosome, a virus, that behaves as an autonomous unit of polynucleotide replication within a cell. That is, it is capable of replication under its own control.

A "vector" is a replicon in which another polynucleotide segment is attached, such as to bring about the replication and/or expression of the attached segment.

The term "control sequence" refers to polynucleotide sequences which are necessary to effect the expression of coding sequences to which they are ligated. The nature of such control sequences differs depending upon the host organism. In prokaryotes, such control sequences generally include promoter, ribosomal binding site and terminators; in eukaryotes, such control sequences generally include promoters, terminators and, in some instances, enhancers. The term "control sequence" thus is intended to include at a minimum all components whose presence is necessary for expression, and also may include additional components whose presence is advantageous, for example, leader sequences.

"Operably linked" refers to a situation wherein the components described are in a relationship permitting them to function in their intended manner. Thus, for example, a control sequence "operably linked" to a coding sequence is ligated in such a manner that expression of the coding sequence is achieved under conditions compatible with the control sequences.

The term "open reading frame" or "ORF" refers to a region of a polynucleotide sequence which encodes a polypeptide; this region may represent a portion of a coding sequence or a total coding sequence.

A "coding sequence" is a polynucleotide sequence which is transcribed into mRNA and/or translated into a polypeptide when placed under the control of appropriate regulatory sequences. The boundaries of the coding sequence are determined by a translation start codon at the 5'-terminus and a translation stop codon at the 3'-terminus. A coding sequence can include, but is not limited to, mRNA and recombinant polypeptide sequences.

The term "immunologically identifiable with/as" refers to the presence of epitope(s) and polypeptide(s) which also are present in and are unique to the designated polypeptide(s), usually mutant HBV proteins. Immunological identity may be determined by antibody binding and/or competition in binding. These techniques are known to the routineer and also are described herein. The uniqueness of an epitope also can be determined by computer searches of known data banks, such as Genbank, for the polynucleotide sequences which encode the epitope, and by amino acid sequence comparisons with other known proteins.

As used herein, "epitope" means an antigenic determinant of a polypeptide. Conceivably, an epitope can comprise three amino acids in a spatial conformation which is unique to the epitope. Generally, an epitope consists of at least five such amino acids, and more usually, it consists of at least 8 to 10 amino acids. Methods of examining spatial conformation are known in the art and include, for example, x-ray crystallography and two-dimensional nuclear magnetic resonance.

A polypeptide is "immunologically reactive" with an antibody when it binds to an antibody due to antibody recognition of a specific epitope contained within the polypeptide. Immunological reactivity may be determined by antibody binding, more particularly by the kinetics of antibody binding, and/or by competition in binding using as competitor(s) a known polypeptide(s) containing an epitope against which the antibody is directed. The methods for determining whether a polypeptide is immunologically reactive with an antibody are known in the art.

As used herein, the term "immunogenic polypeptide containing a mutant HBV epitope" means naturally occurring polypeptides of mutant HBV or fragments thereof, as well as polypeptides prepared by other means, for example, chemical synthesis or the expression of the polypeptide in a recombinant organism.

The term "transformation" refers to the insertion of an exogenous polynucleotide into a host cell, irrespective of the method used for the insertion. For example, direct uptake, transduction, or f-mating are included. The exogenous polynucleotide may be maintained as a non-integrated vector, for example, a plasmid, or alternatively, may be integrated into the host genome.

"Treatment" refers to prophylaxis and/or therapy.

The term "individual" as used herein refers to vertebrates, particularly members of the mammalian species and includes but is not limited to domestic animals, sports animals, primates and humans; more particularly the term refers to chimpanzees and humans.

The term "plus strand" as used herein denotes a nucleic acid that contains the sequence that encodes the polypeptide. The term "minus strand" denotes a nucleic acid that contains a sequence that is complementary to that of the "plus" strand.

"Positive stranded genome" of a virus denotes that the genome is single-stranded and encodes a viral polypeptide(s).

The term "antibody containing body component" (or test sample) refers to a component of an individual's body which is the source of the antibodies of interest. These components are well known in the art. These samples include biological samples which can be tested by the methods of the present invention described herein and include human and animal body fluids such as whole blood, serum, plasma, cerebrospinal fluid, urine, lymph fluids, and various external secretions of the respiratory, intestinal and genitorurinary tracts, tears, saliva, milk, white blood cells, myelomas and the like, biological fluids such as cell culture supernatants, fixed tissue specimens and fixed cell specimens.

"Purified mutant HBV" refers to a preparation of mutant HBV which has been isolated from the cellular constituents with which the virus is normally associated, and from other types of viruses which may be present in the infected tissue. The techniques for isolating viruses are known to those skilled in the art and include, for example, centrifugation and affinity chromatography. A method for the preparation of purified HBV is described herein.

General Uses

After preparing recombinant proteins, synthetic peptides, or purified viral polypeptides of choice as described by the present invention, the recombinant or synthetic peptides can be used to develop unique assays as described herein to detect either the presence of antigen or antibody to mutant HBV. These compositions also can be used to develop monoclonal and/or polyclonal antibodies with a specific recombinant protein or synthetic peptide which specifically bind to the immunological epitope of mutant HBV which is desired by the routineer. Also, it is contemplated that at least one polynucleotide of the invention can be used to develop vaccines by following methods known in the art.

It is contemplated that the reagent employed for the assay can be provided in the form of a kit with one or more containers such as vials or bottles, with each container containing a separate reagent such as a monoclonal antibody, or a cocktail of monoclonal antibodies, or a polypeptide (either recombinant or synthetic) employed in the assay.

"Solid phases" ("solid supports") are known to those in the an and include the walls of wells of a reaction tray, test tubes, polystyrene beads, magnetic beads, nitrocellulose strips, membranes, microparticles such as latex particles, and others. The "solid phase" is not critical and can be selected by one skilled in the art. Thus, latex particles, microparticles, magnetic or non-magnetic beads, membranes, plastic tubes, walls of microtiter wells, glass or silicon chips and sheep red blood cells are all suitable examples. Suitable methods for immobilizing peptides on solid phases include ionic, hydrophobic, covalent interactions and the like. A "solid phase", as used herein, refers to any material which is insoluble, or can be made insoluble by a subsequent reaction. The solid phase can be chosen for its intrinsic ability to attract and immobilize the capture reagent. Alternatively, the solid phase can retain an additional receptor which has the ability to attract and immobilize the capture reagent. The additional receptor can include a charged substance that is oppositely charged with respect to the capture reagent itself or to a charged substance conjugated to the capture reagent. As yet another alternative, the receptor molecule can be any specific binding member which is immobilized upon (attached to) the solid phase and which has the ability to immobilize the capture reagent through a specific binding reaction. The receptor molecule enables the indirect binding of the capture reagent to a solid phase material before the performance of the assay or during the performance of the assay. The solid phase thus can be a plastic, derivatized plastic, magnetic or non-magnetic metal, glass or silicon surface of a test tube, microtiter well, sheet, bead, microparticle, chip, and other configurations known to those of ordinary skill in the art.

It is contemplated and within the scope of the invention that the solid phase also can comprise any suitable porous material with sufficient porosity to allow access by detection antibodies and a suitable surface affinity to bind antigens. Microporous structures are generally preferred, but materials with gel structure in the hydrated state may be used as well. Such useful solid supports include:

natural polymeric carbohydrates and their synthetically modified, cross-linked or substituted derivatives, such as agar, agarose, cross-linked alginic acid, substituted and cross-linked guar gums, cellulose esters, especially with nitric acid and carboxylic acids, mixed cellulose esters, and cellulose ethers; natural polymers containing nitrogen, such as proteins and derivatives, including cross-linked or modified gelatins; natural hydrocarbon polymers, such as latex and rubber; synthetic polymers which may be prepared with suitably porous structures, such as vinyl polymers, including polyethylene, polypropylene, polystyrene, polyvinylchloride, polyvinylacetate and its partially hydrolyzed derivatives, polyacrylamides, polymethacrylates, copolymers and terpolymers of the above polycondensates, such as polyesters, polyamides, and other polymers, such as polyurethanes or polyepoxides; porous inorganic materials such as sulfates or carbonates of alkaline earth metals and magnesium, including barium sulfate, calcium sulfate, calcium carbonate, silicates of alkali and alkaline earth metals, aluminum and magnesium; and aluminum or silicon oxides or hydrates, such as clays, alumina, talc, kaolin, zeolite, silica gel, or glass (these materials may be used as filters with the above polymeric materials); and mixtures or copolymers of the above classes, such as graft copolymers obtained by initializing polymerization of synthetic polymers on a pre-existing natural polymer. All of these materials may be used in suitable shapes, such as films, sheets, or plates, or they may be coated onto or bonded or laminated to appropriate inert carriers, such as paper, glass, plastic films, or fabrics.

The porous structure of nitrocellulose has excellent absorption and adsorption qualities for a wide variety of reagents including monoclonal antibodies. Nylon also possesses similar characteristics and also is suitable. It is contemplated that such porous solid supports described hereinabove are preferably in the form of sheets of thickness from about 0.01 to 0.5 mm, preferably about 0.1 mm. The pore size may vary within wide limits, and is preferably from about 0.025 to 15 microns, especially from about 0.15 to 15 microns. The surfaces of such supports may be activated by chemical processes which cause covalent linkage of the antigen or antibody to the support. The irreversible binding of the antigen or antibody is obtained, however, in general, by adsorption on the porous material by poorly understood hydrophobic forces. Suitable solid supports also are described in U.S. patent application Ser. No. 227,272, which is incorporated herein by reference.

The "indicator reagent" comprises a "signal generating compound" (label) which is capable of generating a measurable signal detectable by external means conjugated (attached) to a specific binding member for mutant HBV. "Specific binding member" as used herein means a member of a specific binding pair. That is, two different molecules where one of the molecules through chemical or physical means specifically binds to the second molecule. In addition to being an antibody member of a specific binding pair for mutant HBV, the indicator reagent also can be a member of any specific binding pair, including either hapten-anti-hapten systems such as biotin or anti-biotin, avidin or biotin, a carbohydrate or a lectin, a complementary nucleotide sequence, an effector or a receptor molecule, an enzyme cofactor and an enzyme, an enzyme inhibitor or an enzyme, and the like. An immunoreactive specific binding member can be an antibody, an antigen, or an antibody/antigen complex that is capable of binding either to mutant HBV as in a sandwich assay, to the capture reagent as in a competitive assay, or to the ancillary specific binding member as in an indirect assay.

The various "signal generating compounds" (labels) contemplated include chromogens, catalysts such as enzymes, luminescent compounds such as fluorescein and rhodamine, chemiluminescent compounds, radioactive elements, and direct visual labels. Examples of enzymes include alkaline phosphatase, horseradish peroxidase, beta-galactosidase, and the like. The selection of a particular label is not critical, but it will be capable of producing a signal either by itself or in conjunction with one or more additional substances.

Other embodiments which utilize various other solid phases also are contemplated and are within the scope of this invention. For example, ion capture procedures for immobilizing an immobilizable reaction complex with a negatively charged polymer, described in co-pending U.S. patent application Ser. No. 150,278 corresponding to EP publication 0326100 and U.S. patent application Ser. No. 375,029 (EP publication no. 0406473), each of which are incorporated herein by reference, can be employed according to the present invention to effect a fast solution-phase immunochemical reaction. An immobilizable immune complex is separated from the rest of the reaction mixture by ionic interactions between the negatively charged poly-anion/immune complex and the previously treated, positively charged porous matrix and detected by using various signal generating systems previously described, including those described in chemiluminescent signal measurements as described in co-pending U.S. patent application Ser. No. 921,979 corresponding to EPO Publication No. 0 273,115, which is incorporated herein by reference.

Also, the methods of the present invention can be adapted for use in systems which utilize microparticle technology including in automated and semi-automated systems wherein the solid phase comprises a microparticle. Such systems include those described in pending U.S. patent applications 425,651 and 425,643, which correspond to published EPO applications Nos. EP 0 425 633 and EP 0 424 634, respectively, which are incorporated herein by reference.

The use of scanning probe microscopy (SPM) for immunoassays also is a technology to which the monoclonal antibodies of the present invention are easily adaptable. In scanning probe microscopy, in particular in atomic force microscopy, the capture phase, for example, at least one of the monoclonal antibodies of the invention, is adhered to a solid phase and a scanning probe microscope is utilized to detect antigen/antibody complexes which may be present on the surface of the solid phase. The use of scanning tunnelling microscopy eliminates the need for labels which normally must be utilized in many immunoassay systems to detect antigen/antibody complexes. Such a system is described in pending U.S. patent application Ser. No. 662,147, which is incorporated herein by reference.

The use of SPM to monitor specific binding reactions can occur in many ways. In one embodiment, one member of a specific binding partner (analyte specific substance which is the monoclonal antibody of the invention) is attached to a surface suitable for scanning. The attachment of the analyte specific substance may be by adsorption to a test piece which comprises a solid phase of a plastic or metal surface, following methods known to those of ordinary skill in the art. Or, covalent attachment of a specific binding partner (analyte specific substance) to a test piece which test piece comprises a solid phase of derivatized plastic, metal, silicon, or glass may be utilized. Covalent attachment methods are known to those skilled in the art and include a variety of means to irreversibly link specific binding partners to the test piece. If the test piece is silicon or glass, the surface must be activated prior to attaching the specific binding partner. Activated silane compounds such as triethoxy amino propyl silane (available from Sigma Chemical Co., St. Louis, Mo.), triethoxy vinyl silane (Aldrich Chemical Co., Milwaukee, Wis.), and (3-mercapto-propyl)-trimethoxy silane (Sigma Chemical Co., St. Louis, Mo.) can be used to introduce reactive groups such as amino-, vinyl, and thiol, respectively. Such activated surfaces can be used to link the binding partner directly (in the cases of amino or thiol) or the activated surface can be further reacted with linkers such as glutaraldehyde, bis (succinimidyl) suberate, SPPD 9 succinimidyl 3-[2-pyridyldithio]propionate), SMCC (succinimidyl-4-[N-maleimidomethyl]cyclohexane-1-carboxylate), SIAB (succinimidyl [4-iodoacetyl]aminobenzoate), and SMPB (succinimidyl 4-[1-maleimidophenyl]butyrate) to separate the binding partner from the surface. The vinyl group can be oxidized to provide a means for covalent attachment. It also can be used as an anchor for the polymerization of various polymers such as poly acrylic acid, which can provide multiple attachment points for specific binding partners. The amino surface can be reacted with oxidized dextrans of various molecular weights to provide hydrophilic linkers of different size and capacity. Examples of oxidizable dextrans include Dextran T-40 (molecular weight 40,000 daltons), Dextran T- 110 (molecular weight 110,000 daltons), Dextran T-500 (molecular weight 500,000 daltons), Dextran T-2M (molecular weight 2,000,000 daltons) (all of which are available from Pharmacia), or Ficoll (molecular weight 70,000 daltons (available from Sigma Chemical Co., St. Louis, Mo.). Also, polyelectrolyte interactions may be used to immobilize a specific binding partner on a surface of a test piece by using techniques and chemistries described by pending U.S. patent applications Ser. No. 150,278, filed Jan. 29, 1988, and Ser. No. 375,029, filed Jul. 7, 1989. The preferred method of attachment is by covalent means. Following attachment of a specific binding member, the surface may be further treated with materials such as serum, proteins, or other blocking agents to minimize non-specific binding. The surface also may be scanned either at the site of manufacture or point of use to verify its suitability for assay purposes. The scanning process is not anticipated to alter the specific binding properties of the test piece.

Various other assay formats may be used, including "sandwich" immunoassays and competitive probe assays. For example, the monoclonal antibodies of the present invention can be employed in various assay systems to determine the presence, if any, of mutant HBV proteins in a test sample. Fragments of these monoclonal antibodies provided also may be used. For example, in a first assay format, a polyclonal or monoclonal anti-mutant HBV antibody or fragment thereof, or a combination of these antibodies, which has been coated on a solid phase, is contacted with a test sample which may contain mutant HBV proteins, to form a mixture. This mixture is incubated for a time and under conditions sufficient to form antigen/antibody complexes. Then, an indicator reagent comprising a monoclonal or a polyclonal antibody or a fragment thereof, which specifically binds to a mutant HBV region, or a combination of these antibodies, to which a signal generating compound has been attached, is contacted with the antigen/antibody complexes to form a second mixture. This second mixture then is incubated for a time and under conditions sufficient to form antibody/antigen/antibody complexes. The presence of mutant HBV antigen present in the test sample and captured on the solid phase, if any, is determined by detecting the measurable signal generated by the signal generating compound. The amount of mutant HBV antigen present in the test sample is proportional to the signal generated.

Alternatively, a polyclonal or monoclonal anti-mutant HBV antibody or fragment thereof, or a combination of these antibodies which is bound to a solid support, the test sample and an indicator reagent comprising a monoclonal or polyclonal antibody or fragments thereof, which specifically binds to mutant HBV antigen, or a combination of these antibodies to which a signal generating compound is attached, are contacted to form a mixture. This mixture is incubated for a time and under conditions sufficient to form antibody/antigen/antibody complexes. The presence, if any, of mutant HBV proteins present in the test sample and captured on the solid phase is determined by detecting the measurable signal generated by the signal generating compound. The amount of mutant HBV proteins present in the test sample is proportional to the signal generated.

In another alternate assay format, one or a combination of one or more monoclonal antibodies of the invention can be employed as a competitive probe for the detection of antibodies to mutant HBV protein. For example, mutant HBV proteins, either alone or in combination with other mutant HBV proteins or non-mutant HBV proteins, can be coated on a solid phase. A test sample suspected of containing antibody to mutant and/or non-mutant HBV antigen then is incubated with an indicator reagent comprising a signal generating compound and at least one monoclonal antibody of the invention for a time and under conditions sufficient to form antigen/antibody complexes of either the test sample and indicator reagent to the solid phase or the indicator reagent to the solid phase. The reduction in binding of the monoclonal antibody to the solid phase can be quantitatively measured. A measurable reduction in the signal compared to the signal generated from a confirmed negative HBV test sample indicates the presence of anti-HBV antibody in the test sample.

In yet another detection method, each of the monoclonal antibodies of the present invention can be employed in the detection of mutant HBV antigens in fixed tissue sections, as well as fixed cells by immunohistochemical analysis.

In addition, these monoclonal antibodies can be bound to matrices similar to CNBr-activated Sepharose and used for the affinity purification of specific mutant HBV proteins from cell cultures, or biological tissues such as blood and liver.

The monoclonal antibodies of the invention can also be used for the generation of chimeric antibodies for therapeutic use, or other similar applications.

The monoclonal antibodies or fragments thereof can be provided individually to detect mutant HBV antigens. Combinations of the monoclonal antibodies (and fragments thereof) provided herein also may be used together as components in a mixture or "cocktail" of at least one anti-mutant HBV antibody of the invention with antibodies to other HBV regions (either mutant or non-mutant, each having different binding specificities. Thus, this cocktail can include the monoclonal antibodies of the invention which are directed to mutant HBV proteins and other monoclonal antibodies to other antigenic determinants of the HBV genome.

The polyclonal antibody or fragment thereof which can be used in the assay formats should specifically bind to a specific region of mutant HBV or other mutant HBV proteins used in the assay. The polyclonal antibody used preferably is of mammalian origin; human, goat, rabbit or sheep anti-HCV polyclonal antibody can be used. Most preferably, the polyclonal antibody is rabbit polyclonal anti-mutant HBV antibody. The polyclonal antibodies used in the assays can be used either alone or as a cocktail of polyclonal antibodies. Since the cocktails used in the assay formats are comprised of either monoclonal antibodies or polyclonal antibodies having different HBV specificity, they would be useful for diagnosis, evaluation and prognosis of HBV infection, as well as for studying HBV protein differentiation and specificity.

In another assay format, the presence of antibody and/or antigen to mutant HBV can be detected in a simultaneous assay, as follows. A test sample is simultaneously contacted with a capture reagent of a first analyte, wherein said capture reagent comprises a first binding member specific for a first analyte attached to a solid phase and a capture reagent for a second analyte, wherein said capture reagent comprises a first binding member for a second analyte attached to a second solid phase, to thereby form a mixture. This mixture is incubated for a time and under conditions sufficient to form capture reagent/first analyte and capture reagent/second analyte complexes. These so-formed complexes then are contacted with an indicator reagent comprising a member of a binding pair specific for the first analyte labelled with a signal generating compound and an indicator reagent comprising a member of a binding pair specific for the second analyte labelled with a signal generating compound to form a second mixture. This second mixture is incubated for a time and under conditions sufficient to form capture reagent/first analyte/indicator reagent complexes and capture reagent/second analyte/indicator reagent complexes. The presence of one or more analytes is determined by detecting a signal generated in connection with the complexes formed on either or both solid phases as an indication of the presence of one or more analytes in the test sample. In this assay format, proteins derived from human expression systems may be utilized as well as monoclonal antibodies produced from the proteins derived from the mammalian expression systems as disclosed herein. Such assay systems are described in greater detail in pending U.S. patent application Ser. No. 07/574,821 entitled Simultaneous Assay for Detecting One Or More Analytes, which corresponds to EP Publication No. 0473065, which is incorporated herein by reference.

In yet other assay formats, recombinant proteins may be utilized to detect the presence of anti-mutant HBV in test samples. For example, a test sample is incubated with a solid phase to which at least one recombinant protein has been attached. These are reacted for a time and under conditions sufficient to form antigen/antibody complexes. Following incubation, the antigen/antibody complex is detected. Indicator reagents may be used to facilitate detection, depending upon the assay system chosen. In another assay format, a test sample is contacted with a solid phase to which a recombinant protein produced as described herein is attached and also is contacted with a monoclonal or polyclonal antibody specific for the protein, which preferably has been labelled with an indicator reagent. After incubation for a time and under conditions sufficient for antibody/antigen complexes to form, the solid phase is separated from the free phase, and the label is detected in either the solid or free phase as an indication of the presence of HBV antibody. Other assay formats utilizing the proteins of the present invention are contemplated. These include contacting a test sample with a solid phase to which at least one recombinant protein produced in the mammalian expression system has been attached, incubating the solid phase and test sample for a time and under conditions sufficient to form antigen/antibody complexes, and then contacting the solid phase with a labelled recombinant antigen. Assays such as this and others are described in pending U.S. patent application Ser. No. 07/787,710, which is incorporated herein by reference.

While the present invention discloses the preference for the use of solid phases, it is contemplated that the proteins of the present invention can be utilized in non-solid phase assay systems. These assay systems are known to those skilled in the art, and are considered to be within the scope of the present invention.

While the present invention discloses the preference for the use of solid phases, it is contemplated that the peptides of the present invention can be utilized in non-solid phase assay systems. These assay systems are known to those skilled in the art, and are considered to be within the scope of the present invention.

Materials and Methods

General Techniques

Conventional and well-known techniques and methods in the fields of molecular biology, microbiology, recombinant DNA and immunology are employed in the practice of the invention unless otherwise noted. Such techniques are explained and detailed in the literature. See, for example, T. Maniatis et at., *Molecular Cloning: A Laboratory Manual,* 2nd edition, Cold Spring Harbor Press, Cold Spring Harbor, N.Y. (1989); D. N. Glover, ed., *DNA Cloning, Volumes I and II* (1985); M. J. Gait ed., *Oligonucleotide Synthesis,* (1984); B. D. Hames et al., eds., *Nucleic Acid Hybridization,* (1984); B. D. Hames et al., eds., *Transcription and Translation,* (1984); R. I. Freshney ed., *Animal Cell Culture,* (1986); *Immobilized Cells and Enzymes,* IRL Press (1986); B. Perbal, *A Practical Guide to Molecular Cloning,* (1984); the series, *Methods in Enzymology,* Academic Press, Inc., Orlando, Fla.; J. H. Miller et al., eds., *Gene Transfer Vectors For Mammalian Cells,* Cold Spring Harbor Laboratory, Cold Spring Harbor, N.Y. (1987); Wu et al., eds., Methods in Enzymology, Vol. 154 and 155; Mayer et al., eds., *Immunological Methods In Cell and Molecular Biology,* Academic Press, London (1987); Scopes, *Protein Purification: Principles and Practice,* 2nd ed., Springer-Verlag, N.Y.; and D. Weir et al., eds., *Handbook Of Experimental Immunology,* Volumes I–IV (1986).

The reagents and methods of the present invention are made possible by the provision of a family of closely homologous nucleotide sequences isolated from a genomic library derived from nucleic acid sequences present in the plasma, serum or liver homogenate of a mutant HBV infected individual. Sera, plasma or liver homogenates from mutant HBV infected humans contain antibodies which bind to this polypeptide, whereas sera, plasma or liver homogenates from non-infected humans do not contain antibodies to this polypeptide. Finally, whereas the sera from uninfected individuals do not contain antibodies to this polypeptide, the antibodies are induced in individuals following acute HBV infection.

The availability of nucleic acid sequences permits the construction of DNA probes and polypeptides useful in diagnosing hepatitis due to mutant HBV infections, and in screening blood donors, donated blood, blood products and individuals for infection. For example, from the sequence it is possible to synthesize DNA oligomers of about eight to ten nucleotides, or larger, which re useful as hybridization probes to detect the presence of the viral genome in, for example, sera of subjects suspected of harboring the virus, or for screening donated blood for the presence of the virus. The family of nucleic acid sequences also allows the design and production of mutant HBV specific polypeptides which are useful as diagnostic reagents for the presence of antibodies raised during infection with mutant HBV. Antibodies to purified polypeptides derived from the nucleic acid sequences may also be used to detect viral antigens in infected individuals and in blood. These nucleic acid sequences also enable the design and production of polypeptides which may be used as vaccines against mutant HBV, and also for the production of antibodies, which then may be used for protection of the disease, and/or for therapy of mutant HBV infected individuals.

The sequences and the polypeptides derived from these sequences, as well as antibodies directed against these polypeptides, also are useful in the isolation and identification of the mutant HBV etiological agent(s). For example, antibodies directed against mutant HBV epitope contained in polypeptides derived from the nucleic acid sequences may be used in methods based upon affinity chromatography to isolate the virus. Alternatively, the antibodies can be used to identify viral particles isolated by other techniques. The viral antigens and the genomic material within the isolated viral particles then may be further characterized.

The information obtained from further sequencing of the mutant HBV genome(s), as well as from further characterization of the mutant HBV antigen and characterization of the genome enables the design and synthesis of additional probes and polypeptides and antibodies which may be used for diagnosis, prevention and therapy of mutant HBV induced hepatitis, and for screening for infected blood and blood-related products.

The availability of probes for mutant HBV, including antigens, antibodies and polynucleotides derived from the genome from which the nucleic acid sequences is derived also allows for the development of tissue culture systems which will be of major use in elucidating the biology of mutant HBV. Once this is known, it is contemplated that new treatment regimens may be developed based upon antiviral compounds which preferentially inhibit the replication of or infection by mutant HBV.

In the method used to identify and isolate the etiological agent of HBV, a genomic library is created from the nucleic acids present in infected serum, plasma or liver homogenates from an infected individual, preferably a chimpanzee or human. The library is created in a vector which allows the expression of polypeptides encoded in the nucleic acid sequences. Clones of host cells containing the vector, which has expressed an immunologically reactive fragment of a polypeptide of the etiological agent (mutant HBV), are selected by immunological screening of the expression products of the library with an antibody containing body component from another individual previously infected with the putative agent. The steps in the immunological screening technique include interacting the expression products of the cloned nucleic acid sequences containing vectors with the antibody containing body component of a second infected individual, and detecting the formation of antigen-antibody complexes between the expression product(s) and antibodies of the second infected individual. The isolated clones are screened further immunologically by interacting their expression products with the antibody containing body component of other individuals infected with the putative agent and detecting the formation of antigen-antibody complexes with antibodies from the infected individuals, and the nucleic acid sequences containing vectors which encode polypeptides which react immunologically with antibodies from infected individuals and individuals suspected of being infected the agent, but not with control individuals, are isolated. The infected individuals used for the construction of the nucleic acid sequence library, and for the immunological screening need not be of the same species. The nucleic acid sequences isolated as a result of this method, and their expression products, and antibodies directed against the expression products, are useful in characterizing and/or capturing the etiological agent. This method is taught in EP Patent Application Publication No. 0 318 216, which is incorporated herein by reference.

Preparation of the Nucleic Acid Sequences

Pooled or individual serum, plasma or liver homogenates from an individual meeting the criteria and within the parameters set forth below with acute or chronic mutant HBV infection is used to isolate viral particles. Nucleic acids isolated from these particles is used as the template in the construction of a genomic library to the viral genome. The procedures used for isolation of mutant HBV particles and for constructing the genomic library in lambda-gt11 or similar systems known in the art is discussed hereinbelow. Lambda-gt11 is a vector that has been developed specifically to express inserted cDNAs as fusion polypeptides with beta-galactosidase and to screen large numbers of recombinant phage with specific antisera raised against a defined antigen. The lambda-gt11 cDNA library generated from a cDNA pool containing cDNA is screened for encoded epitopes that can bind specifically with sera derived from individuals who previously had experienced hepatitis due to mutant HBV. See V. Hunyh et al., in D. Glover, ed, *DNA Cloning Techniques; A Practical Approach*, IRL Press, Oxford, England, pp. 49–78 (1985). Approximately $10^6$–$10^7$ phages are screened, from which positive phages are identified, purified, and then tested for specificity of binding to sera from different individuals previously infected with the mutant HBV agent. Phages which selectively bind sera, plasma from patients meeting the criteria described hereinbelow and not in patients who did not meet these described criteria, are preferred for further study.

By utilizing the technique of isolating overlapping nucleic acid sequences, clones containing additional upstream and downstream mutant HBV sequences are obtained. The isolation of these clones is described hereinbelow.

Analysis of the nucleotide sequences of the mutant HBV nucleic acid sequences encoded within the isolated clones is performed to determine whether the composite sequence contains one long continuous ORF. The sequences (and their complements) retrieved from the mutant HBV library of sequences are provided herein, and the sequences or any portion thereof, can be prepared using synthetic methods or by a combination of synthetic methods with retrieval of partial sequences using methods similar to those described herein. This description thus provides one method by which genomic sequences corresponding to the entire mutant HBV genome may be isolated. Other methods for isolating these sequences, however, will be obvious to those skilled in the art and are considered to be within the scope of the present invention.

Strains replicated from the mutant HBV nucleic acid sequence library will be deposited at the American Type Culture Collection, 12301 Parklawn Drive, Rockville, Md. 20852, under the terms of the Budapest Treaty and will be maintained for a period of thirty (30) years from the date of deposit, or for five (5) years after the last request for the deposit, or for the enforceable period of the U.S. patent, whichever is longer. The deposits and any other deposited material described herein are provided for convenience only, and are not required to practice the present invention in view of the teachings provided herein.

Preparation of Viral Polypeptides and Fragments

The availability of nucleic acid sequences permits the construction of expression vectors encoding antigenically active region of the polypeptide encoded in either strand. The antigenically active region is derived from envelope (coat) antigen. Fragments encoding the desired polypeptides are derived from the genomic clones using conventional restriction digestion or by synthetic methods, and are ligated into vectors which may, for example, contain portions of fusion sequences such as beta-galactosidase (B-gal) or superoxide dismutase (SOD) or CMP-KDO synthetase (CKS). Methods and vectors which are useful for the production of polypeptides which contain fusion sequences of SOD are described in EPO 0196056, published Oct. 1, 1986, and those of CKS are described in EPO Publication No. 0331961, published Sep. 13, 1989, which are incorporated herein by reference. Any desired portion of the nucleic acid sequence containing an open reading frame, in either sense strand, can be obtained as a recombinant protein, such as a mature or fusion protein; alternatively, a polypeptide encoded in the mutant HBV genome can be provided by chemical synthesis.

The nucleic acid sequence encoding the desired polypeptide, whether in fused or mature form, and whether or not containing a signal sequence to permit secretion, may be ligated into expression vectors suitable for any convenient host. Both eucaryotic and prokaryotic host systems are used in the art to form recombinant proteins, and some of these are listed herein. The polypeptide then is isolated from lysed cells or from the culture medium and purified to the extent needed for its intended use. Purification can be performed by techniques known in the art, and include salt fractionation, chromatography on ion exchange resins, affinity chromatography, centrifugation, among others. Such polypeptides may be used as diagnostic reagents, or for passive immunotherapy. In addition, antibodies to these polypeptides are useful for isolating and identifying mutant HBV particles. The mutant HBV antigens also may be isolated from mutant HBV virions. These virions can be grown in mutant HBV infected cells in tissue culture, or in an infected individual.

Preparation of Antigenic Polypeptides and Conjugation With Solid Phase

An antigenic region or fragment of a polypeptide generally is relatively small, usually about 8 to 10 amino acids or less in length. Fragments of as few as 2–5 amino acids may characterize an antigenic region. These segments may correspond to regions of the mutant HBV antigen. By using the mutant HBV genomic sequences as a basis, nucleic acid sequences encoding short segments of mutant HBV polypeptides can be expressed recombinantly either as fusion proteins or as isolated polypeptides. These short amino acid sequences also can be obtained by chemical synthesis. The small chemically synthesized polypeptides may be linked to a suitable carrier molecule when the synthesized polypeptide provided is correctly configured to provide the correct epitope but too small to be antigenic. Linking methods are known in the art and include but are not limited to using N-succinimidyl-3-(2-pyrdylthio)propionate (SPDP) and succinimidyl 4-(N-maleimidomethyl)cyclohexane-1-carboxylate (SMCC). Polypeptides lacking sulfhydryl groups can be modified by adding a cysteine residue. These reagents create a disulfide linkage between themselves and peptide cysteine residues on one protein and an amide linkage through the epsilon-amino on a lysine, or other free amino group in the other. A variety of such disulfide/amide-forming agents are known. Other bifunctional coupling agents form a thioester rather than a disulfide linkage. Many of these thio-ether-forming agents are commercially available and are known to those of ordinary skill in the art. The carboxyl groups can be activated by combining them with succinimide or 1-hydroxyl-2-nitro-4-sulfonic acid, sodium salt. Any carrier which does not itself induce the production of antibodies harmful to the host can be used. Suitable carders include proteins, polysaccharides such as latex functionalized sepharose, agarose, cellulose, cellulose beads, polymeric amino acids such as polyglutamic acid, polylysine, amino acid copolymers and inactive virus particles, among others. Examples of protein substrates include serum albumins, keyhole limpet hemocyanin, immunoglobulin molecules, thyroglobulin, ovalbumin, tetanus toxoid, and yet other proteins known to those skilled in the art.

Preparation of Hybrid Particle Immunogens Containing HBV Epitopes

The immunogenicity of mutant HBV epitope(s) also may be enhanced by preparing them in mammalian or yeast systems fused with or assembled with particle-forming proteins such as those associated with HBV surface antigen. Constructs wherein the mutant HBV epitope is linked directly to the particle-forming protein coding sequences produce hybrids which are immunogenic with respect to the mutant HBV epitope. In addition, all of the vectors prepared include epitopes specific for mutant HBV, having varying degrees of immunogenicity. Particles constructed from particle forming protein which include mutant HBV sequences are immunogenic with respect to mutant HBV.

Hepatitis B surface antigen has been determined to be formed and assembled into particles in *S. cerevisiae* and mammalian cells; the formation of these particles has been reported to enhance the immunogenicity of the monomer subunit. P. Valenzuela et al., *Nature* 298:334 (1982); P. Valenzuela et al., in I. Millman et al., eds., *Hepatitis B*, Plenum Press, pp. 225–236 (1984). The constructs may include immunodominant epitopes of HBsAg. Such constructs have been reported expressible in yeast, and hybrids including heterologous viral sequences for yeast expression have been disclosed. See, for example, EPO 174,444 and EPO 174,261. These constructs also have been reported capable of being expressed in mammalian cells such as Chinese hamster ovary (CHO) cells. Michelle et al., International Symposium on Viral Hepatitis, 1984. In HBV, portions of the particle-forming protein coding sequence may be replaced with codons encoding an HBV epitope. In this replacement, regions that are not required to mediate the aggregation of the units to form immunogenic particles in yeast or mammals can be deleted, thus eliminating additional HBV antigenic sites from competition with the HBV epitope.

Vaccine Preparation

Vaccines may be prepared from one or more immunogenic polypeptides derived from mutant HBV nucleic acid sequences or from the mutant HBV genome to which they correspond. Vaccines may comprise recombinant polypeptides containing epitope(s) of mutant HBV. These polypeptides may be expressed in bacteria, yeast or mammalian cells, or alternatively may be isolated from viral preparations. It also is anticipated that various structural proteins may contain epitopes of mutant HBV which give rise to protective anti-mutant HBV antibodies. Thus, polypeptides containing at least one epitope of mutant HBV may be used, either singly or in combinations, in mutant HBV vaccines. It also is contemplated that nonstructural proteins as well as structural proteins may provide protection against viral pathogenicity, even if they do not cause the production of neutralizing antibodies.

Considering the above, multivalent vaccines against mutant HBV may comprise proteins which include the two amino acid insertion (N-T) at position 122. These vaccines may be comprised of, for example, recombinant mutant HBV polypeptides and/or polypeptides isolated from the virions. Additionally, it may be possible to use inactivated mutant HBV in vaccines. Such inactivation may be by preparation of viral lysates, or by other means known in the art to cause inactivation of hepatitis-like viruses, for example, treatment with organic solvents or detergents, or treatment with formalin. Attenuated mutant HBV strain preparation also is disclosed in the present invention. It is contemplated that some of the proteins in mutant HBV may cross-react with other known viruses, and thus that shared epitopes may exist between mutant HBV and other viruses which would then give rise to protective antibodies against one or more of the disorders caused by these pathogenic agents. It is contemplated that it may be possible to design multiple purpose vaccines based upon this belief.

The preparation of vaccines which contain at least one immunogenic peptide as an active ingredient is known to one skilled in the art. Typically, such vaccines are prepared as injectables, either as liquid solutions or suspensions; solid forms suitable for solution in or suspension in liquid prior to injection also may be prepared. The preparation may be emulsified or the protein may be encapsulated in liposomes. The active immunogenic ingredients often are mixed with pharmacologically acceptable excipients which are compatible with the active ingredient. Suitable excipients include but are not limited to water, saline, dextrose, glycerol, ethanol and the like; combinations of these excipients in various amounts also may be used. The vaccine also may contain small amounts of auxiliary substances such as wetting or emulsifying reagents, pH buffering agents, and/or adjuvants which enhance the effectiveness of the vaccine. For example, such adjuvants can include aluminum hydroxide, N-acetyl-muramyl-L-threonyl-D-isoglutamine (thr-DMP), N-acetyl-nomuramyl-L-alanyl-D-isoglutamine (CGP 11687, also referred to as nor-MDP), N-acetylmuramyul-L-alanyl-D-isoglutaminyl-L-alanine-2-(1'2'-dipalmitoyl-sn-glycero-3-hydroxphosphoryloxy)-ethylamine (CGP 19835A, also referred to as MTP-PE), and RIBI (MPL+TDM+CWS) in a 2% squalene/Tween-80® emulsion. The effectiveness of an adjuvant may be determined by measuring the amount of antibodies directed against an immunogenic polypeptide containing an HBV antigenic sequence resulting from administration of this polypeptide in vaccines which also are comprised of the various adjuvants.

The vaccines usually are administered by intraveneous or intramuscular injection. Additional formulations which are suitable for other modes of administration include suppositories and, in some cases, oral formulations. For suppositories, traditional binders and carders may include but are not limited to polyalkylene glycols or triglycerides. Such suppositories may be formed from mixtures containing the active ingredient in the range of about 0.5% to about 10%, preferably, about 1% to about 2%. Oral formulation include such normally employed excipients as, for example pharmaceutical grades of mannitol, lactose, starch, magnesium stearate, sodium saccharine, cellulose, magnesium carbonate and the like. These compositions may take the form of solutions, suspensions, tablets, pills, capsules, sustained release formulations or powders and contain about 10% to about 95% of active ingredient, preferably about 25% to about 70%.

The proteins used in the vaccine may be formulated into the vaccine as neutral or salt forms. Pharmaceutically acceptable salts such as acid addition salts (formed with free amino groups of the peptide) and which are formed with inorganic acids such as hydrochloric or phosphoric acids, or such organic acids such as acetic, oxalic, tartaric, maleic, and others known to those skilled in the art. Salts formed with the free carboxyl groups also may be derived from inorganic bases such as sodium, potassium, ammonium, calcium or ferric hydroxides and the like, and such organic bases such as isopropylamine, trimethylamine, 2-ethylamino ethanol, histidine procaine, and others known to those skilled in the art.

Vaccines are administered in a way compatible with the dosage formulation, and in such amounts as will be prophylactically and/or therapeutically effective. The quantity to be administered generally is in the range of about 5 micrograms to about 250 micrograms of antigen per dose, and depends upon the subject to be dosed, the capacity of the subject's immune system to synthesize antibodies, and the degree of protection sought. Precise amounts of active ingredient required to be administered also may depend upon the judgment of the practitioner and may be unique to each subject. The vaccine may be given in a single or multiple dose schedule. A multiple dose is one in which a primary course of vaccination may be with one to ten separate doses, followed by other doses given at subsequent time intervals required to maintain and/or to reenforce the immune response, for example, at one to four months for a second dose, and if required by the individual, a subsequent dose(s) after several months. The dosage regimen also will be determined, at least in part, by the need of the individual, and be dependent upon the practitioner's judgment. It is contemplated that the vaccine containing the immunogenic mutant HBV antigen(s) may be administered in conjunction with other immunoregulatory agents, for example, with immune globulins.

Preparation of Antibodies Against Mutant HBV Epitopes

The immunogenic peptides prepared as described herein are used to produce antibodies, either polyclonal or monoclonal. When prepared polyclonal antibodies, a selected mammal (for example, a mouse, rabbit, goat, horse and the like) is immunized with an immunogenic polypeptide bearing at least one mutant HBV epitope. Serum from the immunized animal is collected after an appropriate incubation period and treated according to known procedures. If serum containing polyclonal antibodies to an epitope of mutant HBV contains antibodies to other antigens, the polyclonal antibodies can be purified by, for example, immunoaffinity chromatography. Techniques for producing and processing polyclonal antibodies are known in the art and are described in, among others, Mayer and Walker, eds., *Immunochemical Methods In Cell and Molecular Biology*, Academic Press, London (1987). Polyclonal antibodies also can be isolated. Polyclonal antibodies may be obtained from a mammal previously infected with HBV. An example of a method for purifying antibodies to mutant HBV epitopes from serum of an individual infected with mutant HBV using affinity chromatography is provided herein.

Monoclonal antibodies directed against mutant HBV epitopes also can produced by one skilled in the art. The general methodology for producing such antibodies is well-known and has been described in, for example, Kohler and Milstein, *Nature* 256:494 (1975) and reviewed in J. G. R. Hurrel, ed., *Monoclonal Hybridoma Antibodies: Techniques and Applications*, CRC Press Inc., Boco Ratan, Fla. (1982), as well as that taught by L. T. Mimms et al., *Virology* 176:604–619 (1990). Immortal antibody-producing cell lines can be created by cell fusion, and also by other techniques such as direct transformation of B lymphocytes with oncogenic DNA, or transfection with Epstein-Barr virus. See also, M. Schreier et al., *Hybridoma Techniques,* Scopes (1980) Protein Purification, Principles and Practice, 2nd Edition, Springer-Verlag, New York (1984); Hammerling et al., *Monoclonal Antibodies and T-Cell Hybridomas* (1981 ); Kennet et al., *Monoclonal Antibodies* (1980). Examples of uses and techniques of monoclonal antibodies for HCV are disclosed in U.S. patent applications Ser. Nos. 748,292; 748,563; 610,175, 648,473; 648,477; and 648,475.

Monoclonal and polyclonal antibodies thus developed, directed against mutant HBV epitopes, are useful in diagnostic and prognostic applications, and also, those which are neutralizing are useful in passive immunotherapy. Monoclonal antibodies especially can be used to produce anti-idiotype antibodies. These anti-idiotype antibodies are immunoglobulins which carry an "internal image" of the antigen of the infectious agent against which protection is desired. See, for example, A. Nisonoff et al., *Clin. Immunol. Immunopath.* 21:397–406 (1981), and Dreesman et al., *J. Infect. Dis.* 151:761 (1985). Techniques for raising such idiotype antibodies are known in the all and exemplified, for example, in Grych et al., *Nature* 316:74 (1985); MacNamara et at., *Science* 226:1325 (1984); and Uytdehaag et al., *J. Immunol.* 134:1225 (1985). These anti-idiotypic antibodies also may be useful for treatment of HBV infection, as well as for elucidation of the immunogenic regions of HBV antigens.

Diagnostic Oligonucleotide Probes and Kits

Using determined portions of the isolated mutant HBV nucleic acid sequences as a basis, oligomers of approximately 8 nucleotides or more can be prepared, either by excision or synthetically, which hybridize with the mutant HBV genome and are useful in identification of the viral agent(s)., further characterization of the viral genome, as well as in detection of the virus(es) in diseased individuals. The natural or derived probes for mutant HBV polynucleotides are a length which allows the detection of unique viral sequences by hybridization. While 6 to 8 nucleotides may be a workable length, sequences of 10 to 12 nucleotides are preferred, and those of about 20 nucleotides may be most preferred. These sequences preferably will derive from regions which lack heterogeneity. These probes can be prepared using routine, standard methods including automated oligonucleotide synthetic methods. A complement of any unique portion of the mutant HBV genome will be satisfactory. Complete complementarity is desirable for use as probes, although it may be unnecessary as the length of the fragment is increased.

When used as diagnostic reagents, the biological test sample to be analyzed, such as blood or serum may be treated such as to extract the nucleic acids contained therein. The resulting nucleic acid from the sample may be subjected to gel electrophoresis or other size separation techniques; or, the nucleic acid sample may be dot-blotted without size separation. The probes then are labelled. Suitable labels are methods for attaching labels to probes are known in the art, and include but are not limited to radioactive labels incorporated by nick translation or kinasing, biotin, fluorescent and chemiluminescent probes. Examples of many of these labels are disclosed herein. The nucleic acids extracted from the sample then are treated with the labelled probe under hybridization conditions of suitable stringencies.

The probes can be made completely complementary to the mutant HBV genome. Therefore, usually high stringency conditions are desirable in order to prevent false positives. However, conditions of high stringency should be used only if the probes are complementary to regions of the mutant HBV genome which lack heterogeneity. The stringency of hybridization is determined by a number of factors during the washing procedure, including temperature, ionic strength, length of time and concentration of formamide. See, for example, T. Maniatis (supra). Hybridization can be carried out by a number of various techniques, including, for example, by Ligase Chain Reaction (LCR), Polymerase Chain Reaction (PCR). These techniques are described herein.

It is contemplated that the mutant HBV genome sequences may be present in serum of infected individuals at relatively low levels, for example, approximately $10^2$–$10^3$ sequences per ml. This level may require that amplification techniques be used in hybridization assays, such as the Ligase Chain Reaction or the Polymerase Chain Reaction. Such techniques are known in the art. For example, the "Bio-Bridge" system uses terminal deoxynucleotide transferase to add unmodified 3'-poly-dT-tails to a nucleic acid probe (Enzo Biochem. Corp.). The poly dt-tailed probe is hybridized to the target nucleotide sequence, and then to a biotin-modified poly-A. Also, in EP 124221 there is described a DNA hybridization assay wherein the analyte is annealed to a single-stranded DNA probe that is complementary to an enzyme-labelled oligonucleotide, and the resulting tailed duplex is hybridized to an enzyme-labeled oligonucleotide. EP 2045 10 describes a DNA hybridization assay in which analyte DNA is contacted with a probe that has a tail, such as a poly-dt-tail, an amplifier strand that has a sequence that hybridizes to to the tail of the probe, such as a poly-A sequence, and which is capable of binding a plurality of labelled strands. The technique first may involve amplification of the target HBV sequences in sera to approximately $10^6$ sequences/ml. This may be accomplished by following the methods described by Saiki et al., *Nature* 324:163 (1986). The amplified sequence(s) then may be detected using a hybridization assay such as those known in the art. The probes can be packaged in diagnostic kits which include the probe nucleic acid sequence which sequence may be labelled; alteratively, the probe may be unlabelled and the ingredients for labelling could be included with the kit. The kit also may contain other suitably packaged reagents and materials needed or desirable for the particular hybridization protocol, for example, standards as well as instructions for performing the assay.

Immunoassay and Diagnostic Kits

Both the polypeptides which react immunologically with serum containing mutant HBV antibodies and composites thereof, and the antibodies raised against the mutant HBV specific epitopes in these polypeptides are useful in immunoassays to detect the presence of mutant HBV antibodies, or the presence of the virus and/or viral antigens in biological test samples. The design of these immunoassays is subject to variation, and a variety of these are known in the art; a variety of these have been described herein. The immunoassay may utilize one viral antigen, such as a polypeptide derived from any clone-containing mutant HBV nucleic acid sequence, or from the composite nucleic acid sequences derived from the mutant HBV nucleic acid sequences in these clones, or from the mutant HBV genome from which the nucleic acid sequences in these clones is derived. Or, the immunoassay may use of combination of viral antigens derived from these sources. It may use, for example, a monoclonal antibody directed against the same viral antigen, or polyclonal antibodies directed against different viral antigens. Assays can include but are not limited to those based on competition, direct reaction or sandwich-type assays. Assays may use solid phases or may be performed by immunoprecipitation or any other methods which do not utilize solid phases. Examples of assays which utilize labels as the signal generating compound and those labels are described heroin. Signals also may be amplified by using biotin and avidin, enzyme labels or biotin antiobiotin systems, such as that described in pending U.S. patent application Ser. Nos. 608,849; 070,647; 418,981; and 687,785. Recombinant polypeptides which include epitopes from immunodominant regions of mutant HBV may be useful for the detection of viral antibodies in biological test samples of infected individuals. It also is contemplated that antibodies may be useful in discriminating acute from non-acute infections. Kits suitable for immunodiagnosis and containing the appropriate reagents are constructed by packaging the appropriate materials, including the polypeptides of the invention containing mutant HBV epitopes or antibodies directed against mutant HBV epitopes in suitable containers, along with the remaining reagents and materials required for the conduct of the assay, as well as suitable assay instructions.

Further Characterization of the HBV Genome, Virions, and Viral Antigens Using Probes The mutant HBV nucleic acid sequences may be used to gain further information on the sequence of the mutant HBV genome, and for identification and isolation of mutant HBV. This information, in turn, can lead to additional polynucleotide probes, polypeptides derived from the HBV genome, and antibodies directed against mutant HBV epitopes which would be useful for the diagnosis and/or treatment of mutant HBV hepatitis.

The nucleic acid sequence information is useful for the design of probes for the isolation of additional nucleic acid sequences which are derived from the envelope region of the mutant HBV genome. For example, labelled probes containing a sequence of 8 or more nucleotides, and preferably 20 or more nucleotides, which are derived from regions close to the 5'-termini or 3'-termini of mutant HBV nucleic acid sequences may be used to isolate overlapping nucleic acid sequences from mutant HBV genomic libraries. These sequences which overlap the mutant HBV nucleic acid sequences, but which also contain sequences derived from regions of the genome from which the above-mentioned mutant HBV nucleic acid sequence are not derived, may then be used to synthesize probes for identification of other overlapping fragments which do not necessarily overlap the nucleic acid sequences in the clones. Unless the mutant HBV genome is segmented and the segments lack common sequences, it is possible to sequence the entire viral genome(s) utilizing the technique of isolation of overlapping nucleic acid sequences derived from the viral genome(s). Although it is unlikely, if the genome is a segmented genome which lacks common sequences, the sequence of the genome can be determined serologically by screening lambda-gt11 mutant HBV genomic libraries, sequencing mutant HBV genomic isolates, and using the isolated mutant HBV nucleic acid sequences to isolate overlapping fragments, using the techniques described for the isolation and sequencing of clones. Characterization of the genomic segments alteratively could be from the viral genome(s) isolated from purified mutant HBV particles. Methods for purifying mutant HBV particles and for detecting them during the purification procedure are described herein. Procedures for isolating polynucleotide genomes from vital particles are well-known in the art. The isolated genomic segments then could be cloned and sequenced. Thus, it is possible to clone and sequence the mutant HBV genome(s) irrespective of its nature.

Methods for constructing mutant HBV genomic libraries are known in the art, and vectors useful for this purpose are known in the art. These vectors include lambda-gt11, lambda-gt10, and others. The mutant HBV derived nucleic acid sequence detected by the probes derived from the mutant HBV genomic libraries, may be isolated from the clone by digestion of the isolated polynucleotide with the appropriate restriction enzyme(s), and sequenced.

The sequence information derived from these overlapping mutant HBV nucleic acid sequences is useful for determining areas of homology and heterogeneity within the viral genome(s), which could indicate the presence of different strains of the genome and.or of populations of defective particles. It is also useful for the design of hybridization probes to detect mutant HBV or mutant HBV antigens or mutant HBV nucleic acids in biological samples, and during the isolation of mutant HBV, utilizing the techniques described herein. The overlapping nucleic acid sequences may be used to create expression vectors for polypeptides derived from the mutant HBV genome(s). Encoded within the family of nucleic acid sequences are antigen(s) containing epitopes which are contemplated to be unique to mutant HBV, i.e., antibodies directed against these antigens are absent from individuals infected with HAV, HCV, and HEV, and with the genomic sequences in Genebank are contemplated to indicate that minimal homology exists between these nucleic acid sequences and the polynucleotide sequences of those sources. Thus, antibodies directed against the antigens encoded with the mutant HBV nucleic acid sequences may be used to identify the mutant HBV particle isolated from infected individuals. In addition, they also are useful for the isolation of the mutant HBV agent(s).

Mutant HBV particles may be isolated from the sera of infected individuals or from cell cultures by any of the methods known in the art, including, for example, techniques based on size discrimination such as sedimentation or exclusion methods, or techniques based on density such as ultracentrifugation in density gradients, or precipitation with agents such as polyethylene glycol (PEG), or chromatography on a variety of materials such as anionic or cationic exchange materials, and materials which bind due to hydrophobic interactions, as well as affinity columns. During the isolation procedure the presence of mutant HBV may be detected by hybridization analysis of the extracted genome, using probes derived from mutant HBV nucleic acid sequences or by immunoassay which utilize as probes antibodies directed against mutant HBV antigens encoded within the family of mutant HBV nucleic acid sequences. The antibodies may be polyclonal or monoclonal, and it may be desirable to purify the antibodies before their use in the immunoassay. Such antibodies directed against mutant HBV antigens which are affixed to solid phases are useful for the isolation of mutant HBV by immunoaffinity chromatography. Methods for immunoaffinity chromatography are known in the art, and include methods for affixing antibodies to solid phases so that they retain their immunoselective activity. These methods include adsorption, and covalent binding. Spacer groups may be included in the bifunctional coupling agents such that the antigen binding site of the antibody remains accessible.

During the purification procedure the presence of mutant HBV may be detected and/or verified by nucleic acid hybridization, utilizing as probes polynucleotides derived from a family of HBV genomic sequences, as well as from overlapping mutant HBV nucleic acid sequences. Fractions are treated under conditions which would cause the disruption of viral particles, such as by use of detergents in the presence of chelating agents, and the presence of viral nucleic acid determined by hybridization techniques. Further confirmation that the isolated particles are the agents which induce mutant HBV infection may be obtained by infecting an individual which is preferably a chimpanzee with the isolated virus particles, followed by a determination of whether the symptoms of mutant HBV hepatitis, as described herein, result from the infection.

Determination of polypeptides containing conserved sequences may be useful for selecting probes which bind the mutant HBV genome, thus allowing its isolation. In addition, conserved sequences in conjunction with those derived from the mutant HBV nucleic acid sequences, may be used to design primers for use in systems which amplify genomic sequences. Further, the structure of mutant HBV also may be determined and its components isolated. The morphology and size may be determined by electron microscopy, for example. The identification and localization of specific viral polypeptide antigens such as envelope (coat) antigens, or internal antigens such as nucleic acid binding proteins or core antigens, and polynucleotide polymerase(s) also may be determined by ascertaining whether the antigens are present in major or minor viral components, as well as by utilizing antibodies directed against the specific antigens encoded within isolated nucleic acid sequences as probes. This information may be useful for diagnostic and therapeutic applications. For example, it may be preferable to include an exterior antigen in a vaccine preparation, or perhaps multivalent vaccines may be comprised of a polypeptide derived from the genome encoding a structural protein as well as a polypeptide from another portion of the genome, such as a nonstructural polypeptide.

Cell Culture Systems and Animal Model Systems for Mutant HBV Replication

Generally, suitable cells or cell lines for culturing mutant HBV may include the following: monkey kidney cells such as MK2 and VERO, porcine kidney cell lines such as PS, baby hamster kidney cell lines such as BHK, murine macrophage cell lines such as P388D1, MK1 and Mm1, human macrophage cell lines such as U-937, human peripheral blood leukocytes, human adherent monocytes, hepatocytes or hepatocytic cell lines such as HUH7 and HepG2, embryos or embryonic cell such as chick embryo fibroblasts or cell lines derived from invertebrates, preferably from insects such as drosophia cell lines or more preferably from arthropods such as mosquito cell lines or tick cell lines. It also is possible that primary hepatocytes can be cultured and then infected with mutant HBV. Alternatively, the hepatocyte cultures could be derived from the livers of infected individuals (human or chimpanzee). That latter case is an example of a cell line which is infected in vivo being passaged in vitro. In addition, various immortalization methods can be used to obtain cell lines derived from hepatocyte cultures. For example, primary liver cultures (before and after enrichment of the hepatocyte population) may be fused to a variety of cells to maintain stability. Also, cultures may be infected with transforming viruses, or transfected with transforming genes in order to create permanent or semipermanent cell lines. In addition, cells in liver cultures may be fused to established cell lines such as PehG2. Methods for cell fusion are well-known to the routineer, and include the use of fusion agents such as PEG, Sendai Virus and Epstein-Bart Virus, among others.

It is contemplated that mutant HBV infection of cell lines may be accomplished by techniques such as incubating the cells with viral preparations under conditions which allow viral entry into the cell. It also may be possible to obtain viral production by transfecting the cells with isolated viral polynucleotides. Methods for transfecting tissue culture cells are known in the art and include but are not limited to techniques which use electroporation and precipitation with DEAE-Dextran or calcium phosphate. Transfection with cloned mutant HBV genomic DNA should result in viral replication and the in vitro propagation of the virus. In addition to cultured cells, animal model systems may be used for viral replication.

Screening for Anti-Viral Agents For Mutant HBV

The availability of cell culture and animal model systems for mutant HBV also renders screening for anti-viral agents which inhibit mutant HBV replication possible, and particularly for those agents which preferentially allow cell growth and multiplication while inhibiting viral replication. These screening methods are known in the art. Generally, the anti-viral agents are tested at a variety of concentrations, for their effect on preventing viral replication in cell culture systems which support viral replication, and then for an inhibition of infectivity or of viral pathogenicity, and a low level of toxicity, in an animal model system. The methods and composition provided herein for detecting mutant HBV antigens and mutant HBV polynucleotides are useful for screening of anti-viral agents because they provide an alternative, and perhaps a more sensitive means, for detecting the agent's effect on viral replication than the cell plaque assay or $ID_{50}$ assay. For example, the mutant HBV polynucleotide probes described herein may be used to quantitate the amount of viral nucleic acid produced in a cell culture. This could be performed by hybridization or competition hybridization of the infected cell nucleic acids with a labelled mutant HBV polynucleotide probe. Also, anti-mutant HBV antibodies may be used to identify and quantitate mutant HBV antigen(s) in the cell culture utilizing the immunoassays described herein. Also, since it may be desirable to quantitate mutant HBV antigens in the infected cell culture by a competition assay, the polypeptides encoded within the mutant HBV nucleic acid sequences described herein are useful for these assays. Generally, a recombinant mutant HBV polypeptide derived from the mutant HBV genomic DNA would be labelled, and the inhibition of binding of this labelled polypeptide to a mutant HBV polypeptide due to the antigen produced in the cell culture system would be monitored. These methods are especially useful in cases where the mutant HBV may be able to replicate in a cell lines without causing cell death.

Preparation of Attenuated Strains of Mutant HBV

It maybe possible to isolate attenuated swains of mutant HBV by utilizing the tissue culture systems and/or animal models systems provided herein. These attenuated strains would be useful for vaccines, or for the isolation of viral antigens. Attenuated strains are isolatable after multiple passages in cell culture and/or an animal model. Detection of an attenuated strain in an infected cell or individual is achievable by following methods known in the art and could include the use of antibodies to one or more epitopes encoded in mutant HBV as a probe or the use of a polynucleotide containing an mutant HBV sequence of at least about 8 nucleotides in length as a probe. Also or alternatively, an attenuated strain may be constructed utilizing the genomic information of mutant HBV provided herein, and utilizing recombinant techniques. Usually an attempt is made to delete a region of the genome encoding a polypeptide related to pathogenicity but not to viral replication. The genomic construction would allow the expression of an epitope which gives rise to neutralizing antibodies for mutant HBV. The altered genome then could be used to transform cells which allow mutant HBV replication, and the cells grown under conditions to allow viral replication. Attenuated mutant HBV strains are useful not only for vaccine purposes, but also as sources for the commercial production of viral antigens, since the processing of these viruses would require less stringent protection measures for the employees involved in viral production and/or the production of viral products.

Hosts and Expression Control Sequences

Although the following are known in the art, included herein are general techniques used in extracting the genome from a virus, preparing and probing a genomic library, sequencing clones, constructing expression vectors, transforming cells, performing immunological assays, and for growing cell in culture.

Both procaryotic and eukaryotic host cells may be used for expression of desired coding sequences when appropriate control sequences which are compatible with the designated host are used. Among prokaryotic hosts, *E. coli* is most frequently used. Expression control sequences for prokaryotics include promoters, optionally containing operator portions, and ribosome binding sites. Transfer vectors compatible with prokaryotic hosts are commonly derived from the plasmid pBR322 which contains operons conferring ampicillin and tetracycline resistance, and the various pUC vectors, which also contain sequences conferring antibiotic resistance markers. These markers may be used to obtain successful transformants by selection. Commonly used prokaryotic control sequences include the beta-lactamase (penicillinase), lactose promoter system (Chang et al., *Nature* 198:1056 [1977]) the tryptophan promoter system (reported by Goeddel et al., *Nucleic Acid Res* 8:4057 [1980]) and the lambda-derived P1 promoter and N gene ribosome binding site (Shimatake et al., *Nature* 292:128 [1981]) and the hybrid Tac promoter (De Boer et al., *Proc. Natl. Acad. Sci. USA* 292:128 [1983]) derived from sequences of the trp and lac UV5 promoters. The foregoing systems are particularly compatible with *E. coli;* however, other prokaryotic hosts such as strains of Bacillus or Pseudomonas may be used if desired, with corresponding control sequences.

Eukaryotic hosts include yeast and mammalian cells in culture systems. *Saccharomyces cerevisiae* and *Saccharomyces carlsbergensis* are the most commonly used yeast hosts, and are convenient fungal hosts. Yeast compatible vectors carry markers which permit selection of successful transformants by conferring protrophy to auxotrophic mutants or resistance to heavy metals on wild-type strains. Yeast compatible vectors may employ the 2 micron origin of replication (as described by Broach et al., *Meth. Enz.* 101:307 [1983]), the combination of CEN3 and ARS1 or other means for assuring replication, such as sequences which will result in incorporation of an appropriate fragment into the host cell genome. Control sequences for yeast vectors are known in the art and include promoters for the synthesis of glycolytic enzymes, including the promoter for 3 phosphophycerate kinase. See, for example, Hess et al., *J. Adv. Enzyme Reg.* 7:149 (1968), Holland et al., *Biochemistry* 17:4900 (1978) and Hitzeman *J. Biol. Chem.* 255:2073 (1980). Terminators also may be included, such as those derived from the enolase gene as reported by Holland, *J. Biol. Chem.* 256:1385 (1981). It is contemplated that particularly useful control systems are those which comprise the glyceraldehyde-3 phosphate dehydrogenase (GAPDH) promoter or alcohol dehydrogenase (ADH) regulatable promoter, terminators also derived from GAPDH, and if secretion is desired, leader sequences from yeast alpha factor. In addition, the transcriptional regulatory region and the transcriptional initiation region which are operably linked may be such that they are not naturally associated in the wild-type organism.

Mammalian cell lines available as hosts for expression are known in the art and include many immortalized cell lines which are available from the American Type Culture Collection. These include HeLa cells, Chinese hamster ovary (CHO) cells, baby hamster kidney (BHK) cells, and others. Suitable promoters for mammalian cells also are known in the art and include viral promoters such as that from Simian Virus 40 (SV40), Rous sarcoma virus (RSV), adenovirus (ADV), bovine papilloma virus (BPV), cytomegalovirus (CMV). Mammalian cells also may require terminator sequences and poly A addition sequences; enhancer sequences which increase expression also may be included, and sequences which cause amplification of the gene also may be desirable. These sequences are known in the art. Vectors suitable for replication in mammalian cells may include viral replicons, or sequences which insure integration of the appropriate sequences encoding HBV mutant epitopes into the host genome. An example of a mammalian expression system for HCV is described in U.S. patent application Ser. No. 07/830,024, filed Jan. 31, 1992.

Transformations

Transformation may be by any known method for introducing polynucleotides into a host cell, including packaging the polynucleotide in a virus and transducing a host cell with the virus, and by direct uptake of the polynucleotide. The transformation procedures selected depends upon the host to be transformed. Bacterial transformation by direct uptake generally employs treatment with calcium or rubidium chloride. Cohen, *Proc. Natl. Acad. Sci. USA* 69:2110 (1972). Yeast transformation by direct uptake may be conducted using the calcium phosphate precipitation method of Graham et at., *Virology* 52:526 (1978), or modification thereof.

Vector Construction

Vector construction employs methods known in the art. Generally, site-specific DNA cleavage is performed by treating with suitable restriction enzymes under conditions which generally are specified by the manufacturer of these commercially available enzymes. Usually, about 1 microgram (μg) of plasmid or DNA sequence is cleaved by 1 unit of enzyme in about 20 μl of buffer solution by incubation at 37° C. for 1 to 2 hours. After incubation with the restriction enzyme, protein is removed by phenol/chloroform extraction and the DNA recovered by precipitation with ethanol. The cleaved fragments may be separated using polyacrylamide or agarose gel electrophoresis methods, according to methods known by the routineer.

Sticky end cleavage fragments may be blunt ended using *E. coli* DNA polymerase 1 (Klenow) in the presence of the appropriate deoxynucleotide triphosphates (dNTPs) present in the mixture. Treatment with S1 nuclease also may be used, resulting in the hydrolysis of any single stranded DNA portions.

Ligations are performed using standard buffer and temperature conditions using T4 DNA ligase and ATP. Sticky end ligations require less ATP and less ligase than blunt end ligations. When vector fragments are used as part of a ligation mixture, the vector fragment often is treated with bacterial alkaline phosphatase (BAP) or calf intestinal alkaline phosphatase to remove the 5'-phosphate and thus prevent religation of the vector. Or, restriction enzyme digestion of unwanted fragments can be used to prevent ligation. Ligation mixtures are transformed into suitable cloning hosts such as *E. coli* and successful transformants selected by methods including antibiotic resistance, and then screened for the correct construction.

Construction of Desired DNA Sequences

Synthetic oligonucleotides may be prepared using an automated oligonucleotide synthesizer such as that described by Warner, *DNA* 3:401 (1984). If desired, the synthetic strands may be labelled with $^{32}P$ by treatment with polynucleotide kinase in the presence of $^{32}P$-ATP, using standard conditions for the reaction. DNA sequences including those isolated from genomic or cDNA libraries, may be modified by known methods which include site directed mutagenesis as described by Zoller, *Nucleic Acids Res.* 10:6487 (1982). Briefly, the DNA to be modified is packaged into phage as a single stranded sequence, and converted to a double stranded DNA with DNA polymerase using, as a primer, a synthetic oligonucleotide complementary to the portion of the DNA to be modified, and having the desired modification included in its own sequence. Culture of the transformed bacteria, which contain replications of each strand of the phage, are plated in agar to obtain plaques. Theoretically, 50% of the new plaques contain phage having the mutated sequence, and the remaining 50% have the original sequence. Replicates of the plaques are hybridized to labelled synthetic probe at temperatures and conditions suitable for hybridization with the correct strand, but not with the unmodified sequence. The sequences which have been identified by hybridization are recovered and cloned.

Hybridization With Probe

HBV genomic or DNA libraries may be probed using the procedure described by Grunstein and Hogness, *Proc. Natl. Acad. Sci. USA* 73:3961 (1975). Briefly, the DNA to be probed is immobilized on nitrocellulose filters, denatured and prehybridized with a buffer which contains 0–50% formamide, 0.75M NaCl, 75 mM Na citrate, 0.02% (w/v) each of bovine serum albumin (BSA), polyvinyl pyrollidone and Ficoll, 50 mM Na Phosphate (pH 6.5), 0.1% SDS and 100 µg/ml carrier denatured DNA. The percentage of formamide in the buffer, as well as the time and temperature conditions of the prehybridization and subsequent hybridization steps depends on the stringency required. Oligomeric probes which require lower stringency conditions are generally used with low percentages of formamide, lower temperatures, and longer hybridization times. Probes containing more than 30 or 40 nucleotides such as those derived from genomic sequences generally employ higher temperatures, for example, about 40° to 42° C., and a high percentage, for example, 50% formamide. Following prehybridization, a $^{32}$P-labelled oligonucleotide probe is added to the buffer, and the filters are incubated in this mixture under hybridization conditions. After washing, the treated filters are subjected to autoradiography to show the location of the hybridized probe. DNA in corresponding locations on the original agar plates is used as the source of the desired DNA.

Verification of Construction and Sequencing

For standard vector constructions, ligation mixtures are transformed into *E. coli* swain HB101 or other suitable host, and successful transformants selected by antibiotic resistance or other markers. Plasmids from the transformants then are prepared according to the method of Clewell et al., *Proc. Natl. Acad. Sci. USA* 62:1159 (1969) usually following chloramphenicol amplification as reported by Clewell et al., *J. Bacteriol.* 110:667 (1972). The DNA is isolated and analyzed usually by restriction enzyme analysis and.or sequencing. Sequencing may be by the well-known dideoxy method of Sanger et al., *Proc. Natl. Acad. Sci. USA* 74:5463 (1977) as further described by Messing et al., *Nucleic Acid Res.* 9:309 (1981), or by the method reported by Maxam et al., *Methods in Enzymology* 65:499 (1980). Problems with band compression, which are sometimes observed in GC rich regions, are overcome by use of T-deazoguanosine according to the method reported by Barret al., *Biotechniques* 4:428 (1986).

Enzyme-Linked Immunosorbent Assay

Enzyme-linked immunosorbent assay (ELISA) can be used to measure either antigen or antibody concentrations. This method depends upon conjugation of an enzyme label to either an antigen or antibody, and uses the bound enzyme activity (signal generated) as a quantitative label (measurable generated signal). Methods which utilize enzymes as labels are described herein, as are examples of such enzyme labels.

Preparation of Mutant HBV Nucleic Acid Sequences

The source of the mutant HBV agent is an individual or pooled plasma, serum or liver homogenate from a human or chimpanzee infected with the mutant HBV virus meeting the clinical and laboratory criteria described herein. A chimpanzee alternatively can be experimentally infected with blood from another individual with mutant HBV hepatitis meeting the criteria described hereinbelow. A pool can be made by combining many individual plasma, serum or liver homogenate samples containing high levels of alanine transferase activity; this activity results from hepatic injury due to mutant HBV infection.

For example, a nucleic acid library from plasma, serum or liver homogenate, preferably but not necessarily high titer, is generated as follows. First, viral particles are isolated from the plasma, serum or liver homogenate; then an aliquot is diluted in a buffered solution, such as one containing 50 mM Tris-HCl, pH 8.0, 1 mM EDTA, 100 mM NaCl. Debris is removed by centrifugation, for example, for 20 minutes at 15,000×g at 20° C. Viral particles in the resulting supernatant then are pelleted by centrifugation under appropriate conditions which can be determined routinely by one skilled in the art. To release the viral genome, the particles are disrupted by suspending the pellets in an aliquot of an SDS suspension, for example, one containing 1% SDS, 120 mM EDTA, 10 mM Tris-HCl, pH 7.5, which also contains 2 mg/ml proteinase K, which is followed by incubation at appropriate conditions, for example, 45° C. for 90 minutes. Nucleic acids are isolated by adding, for example, 0.8 μg MS2 bacteriophage RNA as carrier, and extracting the mixture four times with a 1:1 mixture of phenol:chloroform (phenol saturated with 0.5M Tris-HCl, pH 7.5, 0.1% (v/v) beta-mercaptoethanol, 0.1% (w/v) hydroxyquinolone, followed by extraction two times with chloroform. The aqueous phase is concentrated with, for example, 1-butanol prior to precipitation with 2.5 volumes of absolute ethanol overnight at −20° C. Nucleic acids are recovered by centrifugation in, for example, a Beckman SW41 rotor at 40,000 rpm for 90 min at 4° C., and dissolved in water that is treated with 0.05% (v/v) diethylpyrocarbonate and autoclaved.

Nucleic acid obtained by the above procedure is denatured with, for example, 17.5 mM $CH_3HgOH$; cDNA then is synthesized using this denatured nucleic acid as template, and is cloned into the EcoRI site of phage lambda-gt11, for example, by using methods described by Huynh (1985) supra, except that random primers replace oligo(dT) 12–18 during the synthesis of the first nucleic acid strand by reverse transcriptase (see Taylor et al., [1976]).

The lambda-gt11 genomic library generated thusly is screened for epitopes that can bind specifically with serum, plasma or a liver homogenate from an individual who had previously experienced hepatitis due to mutant Hepatitis B Virus (one which meets the criteria as set forth hereinbelow). About $10^4$–$10^7$ phage are screened with sera, plasma, or liver homogenates using the methods of Huyng et at. (supra). Bound human antibody can be detected with sheep anti-human Ig antisera that is radio-labeled with $^{125}I$ or other suitable reporter molecules including HRPO, alkaline phosphatase and others. Positive phages are identified and purified. These phages then are tested for specificity of binding to sera from a pre-determined number of different humans previously infected with the mutant HBV agent, using the same method. Ideally, the phage will encode a polypeptide that reacts with all or a majority of the sera, plasma or liver homogenates that are tested, and will not react with sera, plasma or liver homogenates from individuals who are determined to be "negative" according to the criteria set forth herein for the mutant HBV agent as well as hepatitis A, non-mutant B, C, and E. By following these procedures, a clone that encodes a polypeptide which is specifically recognized immunologically by sera, plasma or liver homogenates from non-A, non-mutant B,non-C, non-E-identified patients.

The present invention will now be described by way of Examples.

EXAMPLES

Example 1. Identification of Serum Samples

Initial Laboratory Determinations

Commercially available immunoassays (AUSZYME® and AUSRIA®II, Abbott Laboratories, Abbott Park, Ill.) were used for the determination of antibody to HBsAg. Following manufacturer's directions, a patient test sample of serum was tested three times by the AUSZYME® assay for antibody to HBsAg. The AUSZYME® kit contains a solid phase (bead) upon which monoclonal antibodies to HBsAg have been coated. The patient test sample tested negative each of the three times for antibody to HBsAg using this test kit. The patient test sample was retested using the AUSRIA®II test kit, which contains a polyclonal antibody to Hepatitis B surface antigen. The results of the AUSRIA®II test indicated that the patient was positive for antibody to HBsAg.

Further Laboratory Testing

A serum test sample from the patient that had tested negative in the AUSZYME® monoclonal antibody test for antibody to HBsAg and positive in the AUSRIA®II polyclonal antibody test for antibody to HBsAg was diluted 1:20. Cross-exchange of AUSRIA®II reagents and AUSZYME® monoclonal reagents was performed (i.e., AUSRIA®II beads with AUSZYME® monoclonal antibody label, and vice versa). The preferred test conditions for evaluation were overnight incubation of the test sample at room temperature for the first incubation and four hours, room temperature for the second incubation. The test sample also was diluted serially, and dilutions were tested and compared with similar dilutions (5-fold) of the positive control. Data from these tests are presented below in Table 1.

TABLE 1

| | AUSTRIA ® II$^{125}$I* Antibody | | | | AUSZYME ® HRP*-Antibody | | | |
|---|---|---|---|---|---|---|---|---|
| | Ausria II Beads | | Auszyme Beads | | Ausria II Beads | | Auszyme Beads | |
| | x cpm | S/C | x cpm | S/C | x 492 | S/C | x 492 | S/C |
| NC | 138 | — | 84 | — | .008 | — | .003 | — |
| PC | 13,782 | 47.5 | 12,548 | 71.1 | .522 | 9.0 | 2.410 | 45.5 |
| Sample | 5,857 | 20.2 | 408 | 2.3 | .087 | 1.5 | .016 | 0.3 |

*$^{125}$I = radioactive I labelled antibody; HRP = Horseradish peroxidase labeled antibody The data previously indicated that the test sample was reactive with AUSRIA®II but not with AUSZYME® monoclonal. The data from Table 1 show that when the cross-exchange of reagents were used for the test sample testing, the test sample was weakly reactive with both combinations, but was somewhat more reactive with AUSZYME® beads and $^{125}$I-antibody than with AUSRIA®II beads and AUSZYME®-HRP antibody. Further investigation of the differences between the antibodies from each test system indicated that the main reactant in the AUSZYME® is an anti-a antibody, as is the HRP-antibody. In AUSRIA®II, the bead is coated with a polyclonal antibody anti-HBs having a strong anti-a, but with anti-d and anti-y capabilities. Further, the $^{125}$I-antibody in AUSRIA®II is a polyclonal which is predominantly anti-a, but both bead and probe antibodies are considered to be broad spectrum. The monoclonal antibody with its focused specificity on anti-a was not reactive with the test sample. Although the test sample reacted with the polyclonal antisera, it was thought that the reactivity of the polyclonal antibody would be altered since it too predominantly detected anti-a. A dilution curve with AUSRIA®II antibody (not shown) revealed that it was in fact altered, although the broad spectrum of the polyclonal reagent was adequate to detect the anti-HBs present in the test sample.

Example 2. Determination of Sequence

Since it was believed that the sample was a form of a mutant HBV, sequencing was performed to determine if any variables were present in the nucleotide and amino acid sequence of HBV surface antigen. The Sanger dideoxy sequencing reaction, as described in T. Maniatis et al., *Molecular Cloning: A Laboratory Manual*, 2nd edition, Cold Spring Harbor Press, Cold Spring Harbor, N.Y., Book 2: Chapter 13, 13.1–13.77 (1989) was performed. Results of sequence determinations showed a two amino acid insertion in the amino acid sequence of the HBsAg at position 122. The nucleotide and amino acid sequence of the mutant HBV are presented in SEQUENCE ID NO. 1 and SEQUENCE ID NO. 2. Repetition of the method revealed slight amino acid changes, and are presented as SEQUENCE ID NO.3 and SEQUENCE ID. NO. 4. What each amino acid sequence has in common is the two amino acid (N-T) insertion at position 122 of HBsAg. Thus there is present in the sequence of HBsAg a modification in which there is an insertion of two amino acids at position 122 (N-T), which modification corresponds to a six nucleotide insertion at position 366 of the HBsAg genome.

The present invention thus provides reagents and methods for determining the presence of mutant HBsAg in a test sample. It is apparent that assaying with a monoclonal antibody test which predominantly utilize anti-a antibodies will not detect this particular mutant. Further, it is predictable based on the data presented that current vaccines will not be protective against this mutant strain of HBV. Thus, reagents of thus mutant HBV are useful for detection of HBV in test samples, and also, for vaccine production. It is contemplated and within the scope of the present invention that a polynucleotide or polypeptide specific for the mutant HBV described herein, or antibodies produced from these polypeptides and polynucleotides, can be combined with present assay reagents and incorporated into current assay procedures for the detection of antibody to HBsAg. Alternatively, these polynucleotide or polypeptide specific for the mutant HBV described herein, or antibodies produced from these polypeptides and polynucleotides, can be used separately for detection of the mutant strain of HBV in which the "a" determinant has a two amino acid insertion at position 122 of the HBsAg sequence.

Other uses or variations of the present invention will be apparent to those of ordinary skill of the art when considering this disclosure. Therefore, the present invention is intended to be limited only by the appended claims.

What is claimed is:

1. A purified polypeptide comprising the sequence of a mutant hepatitis B virus surface antigen (HBsAG) "a" determinant, in which the mutation is insertion of the amino acids Asn and Thr between positions 122 and 123 of the HBsAG sequence.

2. The purified polypeptide of claim 1, produced by expression of a recombinant nucleic acid.

3. The purified polypeptide of claim 1, produced by chemical synthesis.

4. A method for detecting HBV antibodies in a test sample, comprising:
   a. contacting a test sample suspected of having said antibodies with the polypeptide of claim 1, for a time and under conditions sufficient to allow antibody/antigen complexes to form; and
   b. detecting the antibody/antigen complexes which contain the polypeptide.

5. A kit for determining the presence of mutant hepatitis B virus antigen or antibody, comprising a container and the polypeptide of claim 1.

6. The kit of claim 5, wherein the polypeptide is attached to a solid phase.

7. An immunogenic composition comprising the polypeptide of claim 1, optionally linked to a suitable carrier, and a pharmaceutically acceptable excipient.

8. A method for producing antibodies to a mutant hepatitis B virus, comprising administering to a host the composition of claim 7.

9. An isolated or purified immunogenic particle, comprising a polypeptide having an amino acid sequence capable of forming a particle when produced in a host cell, and an epitope of a mutant HBV, wherein said epitope comprises a modified "a" antigenic determinant wherein the modification is insertion of the amino acids Asn and Thr between positions 122 and 123 of the HBsAg sequence.

10. The immunogenic particle of claim 9, wherein the amino acid sequence capable of forming a particle is the amino acid sequence of hepatitis B surface antigen.

11. An immunogenic composition comprising the particle of claim 9 and a pharmaceutically acceptable excipient.

* * * * *

UNITED STATES PATENT AND TRADEMARK OFFICE
CERTIFICATE OF CORRECTION

PATENT NO. : 5,595,739
DATED : January 21, 1997
INVENTOR(S) : Carman et al.

It is certified that error appears in the above-indentified patent and that said Letters Patent is hereby corrected as shown below:

```
On the title page, item [73]
```
In the list of assignees, please add --University of Glasgow, Glasgow, Scotland.--

Signed and Sealed this

Tenth Day of February, 1998

*Attest:*

BRUCE LEHMAN

*Attesting Officer*           *Commissioner of Patents and Trademarks*

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 684 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..684

( x i ) SEQUENCE DESCRIPTION: SEQ ID NO:1:

```
ATG GAG AAC ACC ACA TCA GGA CTC CTA GGA CCC CTG CTC GTG TTA CAG        48
Met Glu Asn Thr Thr Ser Gly Leu Leu Gly Pro Leu Leu Val Leu Gln
1               5                   10                  15

GCG GGG TTT TTC TTG TTG ACA AAA ATC CTC ACA ATA CCA CAG AGT CTA        96
Ala Gly Phe Phe Leu Leu Thr Lys Ile Leu Thr Ile Pro Gln Ser Leu
            20                  25                  30

GAC TCG TGG TGG ACT TCT CTC AGT TTT CTA GGG GGA ACA CCC GTG TGT       144
Asp Ser Trp Trp Thr Ser Leu Ser Phe Leu Gly Gly Thr Pro Val Cys
        35                  40                  45

TCT GGC CAA AAT TCG CAG TCC CAA ATC TCC AGT CAC TCA CCA ACC TGC       192
Ser Gly Gln Asn Ser Gln Ser Gln Ile Ser Ser His Ser Pro Thr Cys
    50                  55                  60

TGT CCT CCA ATT TGT CCT GGT TAT CGC TGG ATG TGT CTG CGG CGT TTT       240
Cys Pro Pro Ile Cys Pro Gly Tyr Arg Trp Met Cys Leu Arg Arg Phe
65                  70                  75                  80

ATC ATC TTC CTC TGC ATC CTG CTA TGC CTC ATC TTC TTG TTG GTT           288
Ile Ile Phe Leu Cys Ile Leu Leu Leu Cys Leu Ile Phe Leu Leu Val
                85                  90                  95

CCT CTG GAC TAC CAA GGT ATG TTG CCC GTT TGT CCT CTA ATT CCA GGA       336
Leu Leu Asp Tyr Gln Gly Met Leu Pro Val Cys Pro Leu Ile Pro Gly
            100                 105                 110

TCA TCA ACA ACC AGC ACC GGA CCA TGC AGG AAC ACA ACC TGC ACG ACT       384
Ser Ser Thr Thr Ser Thr Gly Pro Cys Arg Asn Thr Thr Cys Thr Thr
        115                 120                 125

CCT GCT CAA GGA ACC TCT ATG TTT CCC TCA TGT TGC TGT ACA AAA CCT       432
Pro Ala Gln Gly Thr Ser Met Phe Pro Ser Cys Cys Cys Thr Lys Pro
    130                 135                 140

ACC GAC AGA AAC TGC ACC TGT ATT CCC ATC CCA TCA TCT TGG GCT TTC       480
Thr Asp Arg Asn Cys Thr Cys Ile Pro Ile Pro Ser Ser Trp Ala Phe
145                 150                 155                 160

GCA AAA TTC CTA TGG GAG TGG GCC TCA GTC CGT TTC TCT TGG CTC AGT       528
Ala Lys Phe Leu Trp Glu Trp Ala Ser Val Arg Phe Ser Trp Leu Ser
                165                 170                 175

TTA CTA GTG CCA TTT GTT CAG TGG TTC GTA GGG CTT TCC CCC ACT GTC       576
Leu Leu Val Pro Phe Val Gln Trp Phe Val Gly Leu Ser Pro Thr Val
            180                 185                 190

TGG CTT TCA GTT ATA TGG ATG ATG TGG TAT TGG GGG CCA AGT CTG TAC       624
Trp Leu Ser Val Ile Trp Met Met Trp Tyr Trp Gly Pro Ser Leu Tyr
        195                 200                 205

AAC ATC TTG AGT CCC TTT ATG CCG CTG TTA CCA ATT TTC TAT TGT CTT       672
Asn Ile Leu Ser Pro Phe Met Pro Leu Leu Pro Ile Phe Tyr Cys Leu
    210                 215                 220
```

```
TGG GTA TAC ATT                                                                    684
Trp Val Tyr Ile
225
```

( 2 ) INFORMATION FOR SEQ ID NO:2:

( i ) SEQUENCE CHARACTERISTICS:
        ( A ) LENGTH: 228 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:2:

```
Met Glu Asn Thr Thr Ser Gly Leu Leu Gly Pro Leu Leu Val Leu Gln
1               5                   10                  15

Ala Gly Phe Phe Leu Leu Thr Lys Ile Leu Thr Ile Pro Gln Ser Leu
            20                  25                  30

Asp Ser Trp Trp Thr Ser Leu Ser Phe Leu Gly Gly Thr Pro Val Cys
        35                  40                  45

Ser Gly Gln Asn Ser Gln Ser Gln Ile Ser Ser His Ser Pro Thr Cys
    50              55                  60

Cys Pro Pro Ile Cys Pro Gly Tyr Arg Trp Met Cys Leu Arg Arg Phe
65              70                  75                  80

Ile Ile Phe Leu Cys Ile Leu Leu Leu Cys Leu Ile Phe Leu Leu Val
                85                  90                  95

Leu Leu Asp Tyr Gln Gly Met Leu Pro Val Cys Pro Leu Ile Pro Gly
            100                 105                 110

Ser Ser Thr Thr Ser Thr Gly Pro Cys Arg Asn Thr Thr Cys Thr Thr
            115                 120                 125

Pro Ala Gln Gly Thr Ser Met Phe Pro Ser Cys Cys Cys Thr Lys Pro
    130                 135                 140

Thr Asp Arg Asn Cys Thr Cys Ile Pro Ile Pro Ser Ser Trp Ala Phe
145                 150                 155                 160

Ala Lys Phe Leu Trp Glu Trp Ala Ser Val Arg Phe Ser Trp Leu Ser
                165                 170                 175

Leu Leu Val Pro Phe Val Gln Trp Phe Val Gly Leu Ser Pro Thr Val
            180                 185                 190

Trp Leu Ser Val Ile Trp Met Met Trp Tyr Trp Gly Pro Ser Leu Tyr
        195                 200                 205

Asn Ile Leu Ser Pro Phe Met Pro Leu Leu Pro Ile Phe Tyr Cys Leu
    210                 215                 220

Trp Val Tyr Ile
225
```

( 2 ) INFORMATION FOR SEQ ID NO:3:

( i ) SEQUENCE CHARACTERISTICS:
        ( A ) LENGTH: 228 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:3:

```
Met Glu Asn Thr Thr Ser Gly Leu Leu Gly Pro Leu Leu Val Leu Gln
1               5                   10                  15

Ala Gly Phe Phe Leu Leu Thr Lys Ile Leu Thr Ile Pro Gln Ser Leu
            20                  25                  30
```

```
Asp Ser Trp Trp Thr Ser Leu Ser Phe Leu Gly Gly Thr Pro Val Cys
        35                  40                  45
Phe Gly Gln Asn Ser Gln Thr Gln Ile Ser Ser His Ser Pro Thr Cys
    50                  55                  60
Cys Pro Pro Ile Cys Pro Gly Tyr Arg Trp Met Cys Leu Arg Arg Phe
65                  70                  75                      80
Ile Ile Phe Leu Cys Ile Leu Leu Leu Cys Leu Ile Phe Leu Leu Val
                85                  90                  95
Leu Leu Asp Tyr Gln Gly Met Leu Pro Val Cys Pro Leu Ile Pro Gly
            100                 105                 110
Ser Ser Thr Thr Ser Thr Gly Pro Cys Arg Asn Thr Thr Cys Thr Thr
        115                 120                 125
Pro Ala Gln Gly Thr Ser Met Phe Pro Ser Cys Cys Cys Thr Lys Pro
    130                 135                 140
Thr Asp Arg Asn Cys Thr Cys Ile Pro Ile Pro Ser Ser Trp Ala Phe
145                 150                 155                     160
Val Lys Phe Leu Trp Glu Trp Ala Ser Val Arg Phe Ser Trp Leu Ser
                165                 170                 175
Phe Leu Val Pro Ile Val Gln Trp Phe Ala Gly Leu Ser Pro Thr Val
            180                 185                 190
Trp Leu Ser Val Ile Trp Met Met Trp Tyr Trp Gly Pro Ser Leu Tyr
        195                 200                 205
Asn Ile Leu Ser Pro Phe Met Pro Leu Leu Pro Ile Phe Tyr Cys Leu
210                 215                 220
Trp Val Tyr Ile
225
```

(2) INFORMATION FOR SEQ ID NO:4:

(i) SEQUENCE CHARACTERISTICS:
        (A) LENGTH: 228 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

```
Met Glu Asn Thr Thr Ser Gly His Leu Thr His Leu Leu Val Leu Gln
1               5                   10                  15
Ala Gly Phe Phe Leu Leu Thr Lys Ile Leu Thr Ile Pro Gln Ser Leu
            20                  25                  30
Asp Ser Trp Trp Thr Ser Leu Ser Phe Leu Gly Gly Thr Pro Val Cys
        35                  40                  45
Ser Gly Gln Asn Ser Gln Ser Gln Ile Ser Ser His Ser Pro Thr Cys
    50                  55                  60
Ser Pro Pro Ile Cys Pro Gly Tyr Arg Trp Met Cys Leu Arg Arg Phe
65                  70                  75                      80
Ile Ile Phe Leu Cys Ile Leu Leu Leu Cys Leu Ile Phe Leu Leu Val
                85                  90                  95
Leu Leu Asp Tyr Gln Gly Met Leu Pro Val Cys Pro Leu Ile Pro Gly
            100                 105                 110
Ser Ser Thr Thr Ser Thr Gly Pro Cys Arg Asn Thr Thr Cys Thr Thr
        115                 120                 125
Pro Ala Gln Gly Thr Ser Met Phe Pro Ser Cys Cys Cys Thr Lys Pro
    130                 135                 140
```

| | | | | | | | | | | | | | | |
|---|---|---|---|---|---|---|---|---|---|---|---|---|---|---|
| Thr 145 | Asp | Arg | Asn | Cys | Thr 150 | Cys | Leu | Pro | Pro 155 | Ser | Ser | Trp | Ala | Phe 160 |
| Ala | Lys | Phe | Leu | Trp 165 | Glu | Trp | Ala | Ser | Val 170 | Gly | Phe | Ser | Trp | Leu 175 | Ser |
| Leu | Leu | Val | Pro 180 | Phe | Val | Gln | Trp | Phe 185 | Val | Gly | Phe | Pro | Pro 190 | Thr | Val |
| Trp | Leu | Ser 195 | Val | Ile | Trp | Met | Met 200 | Trp | Tyr | Trp | Gly | Pro 205 | Ser | Leu | Tyr |
| Asn | Ile 210 | Leu | Ser | Pro | Phe | Met 215 | Pro | Leu | Leu | Pro | Ile 220 | Phe | Tyr | Cys | Leu |
| Trp 225 | Val | Tyr | Ile | | | | | | | | | | | |